(12) United States Patent
Poulsen et al.

(10) Patent No.: US 9,034,818 B2
(45) Date of Patent: May 19, 2015

(54) PHARMACEUTICAL FORMULATIONS COMPRISING AN INSULIN DERIVATIVE

(75) Inventors: Christian Poulsen, København K (DK); Kasper Huus, København V (DK); Frantisek Hubalek, Herlev (DK); Dorte Bjerre Steensgaard, Københabn Ø (DK); Svend Havelund, Bagsværd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/664,156

(22) PCT Filed: Jun. 12, 2008

(86) PCT No.: PCT/EP2008/057413
§ 371 (c)(1),
(2), (4) Date: Feb. 12, 2010

(87) PCT Pub. No.: WO2008/152106
PCT Pub. Date: Dec. 18, 2008

(65) Prior Publication Data
US 2010/0167990 A1    Jul. 1, 2010

Related U.S. Application Data

(60) Provisional application No. 60/934,652, filed on Jun. 15, 2007.

(30) Foreign Application Priority Data

Jun. 13, 2007    (EP) ..................... 07110176

(51) Int. Cl.
| | | |
|---|---|---|
| A61K 38/28 | (2006.01) | |
| A61K 9/00 | (2006.01) | |
| C07K 14/62 | (2006.01) | |
| A61K 9/08 | (2006.01) | |
| A61K 31/315 | (2006.01) | |
| A61K 33/30 | (2006.01) | |
| A61K 45/06 | (2006.01) | |
| A61K 47/10 | (2006.01) | |
| A61K 47/12 | (2006.01) | |
| A61K 47/18 | (2006.01) | |

(52) U.S. Cl.
CPC ............... *A61K 9/0019* (2013.01); *C07K 14/62* (2013.01); *A61K 9/08* (2013.01); *A61K 31/315* (2013.01); *A61K 33/30* (2013.01); *A61K 38/28* (2013.01); *A61K 45/06* (2013.01); *A61K 47/10* (2013.01); *A61K 47/12* (2013.01); *A61K 47/18* (2013.01); *A61K 47/183* (2013.01)

(58) Field of Classification Search
CPC ................................ A61K 38/28; C07K 14/62
See application file for complete search history.

(56) References Cited

U.S. PATENT DOCUMENTS

| | | | |
|---|---|---|---|
| 3,528,960 A | 9/1970 | Haas | |
| 3,868,358 A | 2/1975 | Jackson | |
| 4,476,118 A * | 10/1984 | Brange et al. .................. | 514/6.4 |
| 5,177,058 A | 1/1993 | Dorschug | |
| 5,382,574 A | 1/1995 | Jorgensen | |
| 5,605,884 A | 2/1997 | Lee et al. | |
| 5,646,242 A | 7/1997 | Baker et al. | |
| 5,750,497 A | 5/1998 | Havelund et al. | |
| 5,830,999 A | 11/1998 | Dunn | |
| 5,866,538 A | 2/1999 | Norup et al. | |
| 5,898,067 A | 4/1999 | Balschmidt et al. | |
| 5,905,140 A | 5/1999 | Hansen | |
| 6,011,007 A | 1/2000 | Havelund et al. | |
| 6,174,856 B1 | 1/2001 | Langballe et al. | |
| 6,211,144 B1 | 4/2001 | Havelund | |
| 6,221,837 B1 | 4/2001 | Ertl et al. | |
| 6,251,856 B1 | 6/2001 | Markussen et al. | |
| 6,335,316 B1 | 1/2002 | Hughes et al. | |
| 6,451,762 B1 * | 9/2002 | Havelund et al. .............. | 514/6.3 |
| 6,451,970 B1 | 9/2002 | Schaffer et al. | |
| 6,504,005 B1 | 1/2003 | Fridkin et al. | |
| 6,620,780 B2 | 9/2003 | Markussen et al. | |
| 6,652,886 B2 | 11/2003 | Ahn et al. | |
| 6,869,930 B1 | 3/2005 | Havelund et al. | |
| 7,229,964 B2 | 6/2007 | Markussen et al. | |
| 7,402,565 B2 | 7/2008 | Kjeldsen et al. | |
| 7,544,656 B2 | 6/2009 | Sabetsky | |
| 7,615,532 B2 | 11/2009 | Jonassen et al. | |
| 8,003,605 B2 | 8/2011 | Bayer et al. | |
| 8,067,362 B2 | 11/2011 | Kodra et al. | |
| 2002/0045731 A1 | 4/2002 | Schaeffer et al. | |

(Continued)

FOREIGN PATENT DOCUMENTS

| | | |
|---|---|---|
| AU | 2011252127 B2 | 2/2014 |
| CN | 101389650 | 3/2009 |

(Continued)

OTHER PUBLICATIONS

Jonassen, I. et al., Pharmaceutical Research 2006, vol. 23, No. 1, pp. 49-55.

(Continued)

*Primary Examiner* — Gyan Chandra
(74) *Attorney, Agent, or Firm* — Rosemarie R. Wilk-Orescan

(57) ABSTRACT

The invention concerns a soluble pharmaceutical formulation comprising an insulin derivative wherein the formulation further comprises more than 4 zinc atoms per 6 molecules of the insulin derivative, and a citric acid monohydrate and/or a histidine compound used in an amount sufficient to increase the tendency of the insulin derivative to self-associate into dodecamers. The invention further comprises a process for preparing the soluble pharmaceutical formulation.

14 Claims, 6 Drawing Sheets

(56) References Cited

U.S. PATENT DOCUMENTS

| | | |
|---|---|---|
| 2002/0155994 A1 | 10/2002 | Havelund et al. |
| 2003/0004096 A1 | 1/2003 | Boderke |
| 2003/0236196 A1 | 12/2003 | Kerwin et al. |
| 2004/0006000 A1 | 1/2004 | Langkjaer |
| 2004/0116345 A1 | 6/2004 | Besman et al. |
| 2004/0138099 A1 | 7/2004 | Draeger |
| 2005/0054818 A1 | 3/2005 | Brader et al. |
| 2005/0074866 A1 | 4/2005 | Grancha et al. |
| 2005/0222006 A1 | 10/2005 | Havelund et al. |
| 2005/0232899 A1 | 10/2005 | Balwani et al. |
| 2006/0183668 A1 | 8/2006 | Jonassen et al. |
| 2008/0076705 A1 | 3/2008 | Kodra et al. |
| 2009/0137454 A1 | 5/2009 | Fynbo et al. |
| 2009/0239785 A1 | 9/2009 | Hubalek et al. |
| 2009/0312236 A1 | 12/2009 | Beals et al. |
| 2010/0009899 A1 | 1/2010 | Jonassen et al. |
| 2010/0167990 A1 | 7/2010 | Poulsen et al. |
| 2011/0152185 A1 | 6/2011 | Plum et al. |

FOREIGN PATENT DOCUMENTS

| | | |
|---|---|---|
| DE | 1212679 B | 3/1966 |
| EP | 214826 A2 | 3/1987 |
| EP | 315968 A1 | 5/1989 |
| EP | 375437 A2 | 6/1990 |
| EP | 383472 A2 | 8/1990 |
| EP | 420649 A2 | 4/1991 |
| EP | 818204 A2 | 1/1998 |
| EP | 925792 | 6/1999 |
| EP | 1153608 A1 | 11/2001 |
| EP | 1283051 A1 | 2/2003 |
| EP | 894095 | 5/2003 |
| EP | 1595544 | 11/2005 |
| EP | 2107069 A2 | 10/2009 |
| EP | 2264065 | 12/2010 |
| EP | 2264066 | 12/2010 |
| EP | 2275439 | 1/2011 |
| EP | 2287184 | 2/2011 |
| EP | 2505593 A1 | 10/2012 |
| GB | 1042194 A | 9/1966 |
| GB | 1492997 | 11/1977 |
| JP | B S36-11994 | 7/1961 |
| JP | B S38-5689 | 5/1963 |
| JP | 57-067548 | 4/1982 |
| JP | 1254699 | 10/1989 |
| JP | 5026567 A | 2/1993 |
| JP | 9-502867 | 3/1997 |
| JP | 10-509176 | 9/1998 |
| JP | 11-502110 | 2/1999 |
| JP | 2000-501419 | 2/2000 |
| JP | 2000-504732 | 4/2000 |
| JP | 2000-515542 | 11/2000 |
| JP | 2001-518915 | 10/2001 |
| JP | 2001-518916 A | 10/2001 |
| JP | 2001-521004 | 11/2001 |
| JP | 2001-521006 | 11/2001 |
| JP | 2001-521904 | 11/2001 |
| JP | 2001-526225 A | 12/2001 |
| JP | 2002-527487 | 8/2002 |
| JP | 2002-308899 | 10/2002 |
| JP | 2002-543092 | 12/2002 |
| JP | 2004-523589 | 8/2004 |
| JP | 2006-511441 A | 4/2006 |
| JP | 2006-519253 | 8/2006 |
| JP | 2007-523881 | 8/2007 |
| JP | 2009/522231 A | 6/2009 |
| JP | 4808785 B2 | 11/2011 |
| JP | 5331071 B2 | 10/2013 |
| RU | 2160118 C2 | 12/2000 |
| RU | 2164520 C2 | 3/2001 |
| RU | 2317821 C2 | 2/2008 |
| RU | 2352581 | 4/2009 |
| WO | 91/09617 A1 | 7/1991 |
| WO | WO 91/12817 | 9/1991 |
| WO | 93/12812 A1 | 7/1993 |
| WO | WO 95/07931 | 3/1995 |
| WO | 95/32730 A1 | 12/1995 |
| WO | 96/10417 A1 | 4/1996 |
| WO | 96/29344 | 9/1996 |
| WO | 97/04801 A1 | 2/1997 |
| WO | WO 97/31022 | 8/1997 |
| WO | WO 98/02460 | 1/1998 |
| WO | 98/05361 | 2/1998 |
| WO | WO 98/05361 | 2/1998 |
| WO | 98/42368 A1 | 10/1998 |
| WO | 98/47529 A1 | 10/1998 |
| WO | WO 98/42367 | 10/1998 |
| WO | WO 99/21888 | 5/1999 |
| WO | WO 99/24071 | 5/1999 |
| WO | 99/32116 A1 | 7/1999 |
| WO | WO 00/23098 | 4/2000 |
| WO | 00/43034 A2 | 7/2000 |
| WO | 00/64940 | 11/2000 |
| WO | 01/49314 A2 | 7/2001 |
| WO | WO 02/076495 | 10/2002 |
| WO | 03/002136 A2 | 1/2003 |
| WO | 03/013573 | 2/2003 |
| WO | 03/053339 A2 | 7/2003 |
| WO | WO 03/053339 | 7/2003 |
| WO | 03/094951 A1 | 11/2003 |
| WO | 03/094956 A1 | 11/2003 |
| WO | 2004/039392 A2 | 5/2004 |
| WO | 2004/112828 A1 | 12/2004 |
| WO | 2005/005477 A2 | 1/2005 |
| WO | 2005/012347 A2 | 2/2005 |
| WO | 2005/016365 A2 | 2/2005 |
| WO | 2005/021022 A2 | 3/2005 |
| WO | 2005/047508 A1 | 5/2005 |
| WO | 2005/063298 A1 | 7/2005 |
| WO | 2005/089722 A1 | 9/2005 |
| WO | 2005/117948 A1 | 12/2005 |
| WO | WO 2006/008238 | 1/2006 |
| WO | 2006/020720 A2 | 2/2006 |
| WO | 2006/023665 A2 | 3/2006 |
| WO | 2006/051103 A2 | 5/2006 |
| WO | 2006/053906 A1 | 5/2006 |
| WO | 2006/079019 A2 | 7/2006 |
| WO | 2006/082204 | 8/2006 |
| WO | 2006/082205 | 8/2006 |
| WO | WO 2007/041481 | 4/2007 |
| WO | WO 2007/074133 | 7/2007 |
| WO | 2007/096431 A1 | 8/2007 |
| WO | 2007/121256 A2 | 10/2007 |
| WO | 2007/128815 A1 | 11/2007 |
| WO | 2007/128817 A2 | 11/2007 |
| WO | WO 2007/135117 | 11/2007 |
| WO | 2008/034881 A1 | 3/2008 |
| WO | WO 2008/152106 | 12/2008 |
| WO | WO 2009/060071 | 5/2009 |
| WO | WO 2009/063072 | 5/2009 |
| WO | WO 2010/049488 | 5/2010 |
| WO | 2011/141407 | 11/2011 |

OTHER PUBLICATIONS

Annual Review Endocrine Metabolism 2000, pp. 46-53.
Machine Translation of Japanese Patent 10-509176, published Sep. 8, 1998.
Machine Translation of Japanese Patent 11-502110, published Feb. 23, 1999.
Machine Translation of Japanese Patent 2000-501419, published Feb. 8, 2000.
Machine Translation of Japanese Patent 2000-504732, published Apr. 18, 2000.
Machine Translation of Japanese Patent 2001-521004, published Nov. 6, 2001.
Machine Translation of Japanese Patent 2001-521904, published Nov. 13, 2001.
Machine Translation of Japanese Patent 2002-543092, published Dec. 17, 2002.
Machine Translation of Japanese Patent 2002-308899, published Oct. 23, 2002.

(56) References Cited

OTHER PUBLICATIONS

Machine Translation of Japanese Patent 9-502867, published Mar. 25, 1997.
Machine Translation of Japanese Patent 2001-521006, published Nov. 6, 2001.
Abstract of Japanese Patent 57-067548, published Apr. 24, 1982.
Abstract of Japanese Patent 1254699, published Oct. 11, 1989.
Barnett, A.H., "A Review of Basal Insulins," Diabet Med, 2003, vol. 20, No. 11, pp. 873-885.
Brussels: International Diabetes Federation, IDF Clinical Guidelines Task Force, Guideline for Management of Postmeal Glucose, 2007, pp. 1-32, http://www.idf.org/webdata/docs/Guideline_PMG_final.pdf.
Brussels: International Diabetes Federation, IDF Clinical Guidelines Task Force, Global Guideline for Type 2 Diabetes, 2005, pp. 1-82, http://www.idf.org/webdata/docs/IDF%20GGT2D.pdf.
Definition of Moiety From http://dictionary.reference.com/browse/moiety, 2010, pp. 1-3.
Heise, T. et al., "Towards Peakless, Reporducible and Long-Acting Insulins. An Assessment of the Basal Analogues Based on Isoglycaemic Clamp Studies," Diabetes Obes Metab, 2007, vol. 9, No. 5, pp. 648-659.
Hinds et al., "Pegylated Insulin in PLGA Microparticles. In Vivo and In Vitro Analysis," J Control Release, 2005, vol. 104, No. 3, pp. 447-460.
Irie et al., "Pharmacokinetics and Pharmacodynamics of Single Dose Insulin Detemir, Long-Acting Soluble Insulin Analogue Compared to NPH Insulin in Patients With Type 1 Diabetes Mellitus", J Clin Ther Med, 2007, vol. 23, No. 5, pp. 349-356.
Machine Translation CN 101389650, published Mar. 18, 2009.
Machine Translation of JP 2000-515542, published Nov. 21, 2000.
Machine Translation of JP 2006-519253, published Aug. 24, 2006.
Machine Translation of JP 2007-523881, published Aug. 23, 2007.
Nathan, D.M. et al., "Management for Hyperglycemia in Type 2 Diabetes Consensus Algorithm for the Initiation and Adjustment of Therapy," Diabetes Care, 2008, vol. 31, No. 1, pp. 173-175.
Vajo et al., "Genetically Engineered Insulin Analogs: Diabetes in the New Millennium," Pharma Rev, 2000, vol. 52, No. 1, pp. 1-9.
Samuel et al. "Studies on the immunogenicity of protamines in humans and experimental animals by means of a micro-complement fixation test." Clin. Exp. Immunol. vol. 33: pp. 252-260. 1978.
Kurtz et al. "Circulating IgG antibody to protamine in patients treated with protamine-insulins." Diabetologica. vol. 25: pp. 322-324. 1983.
Heller. S R, Current Medical Research and Opinion, "Insulin Analogues", 2002, vol. 18, No. 1, pp. 40-47.
I. Jonassen et al., Diabetologia, "Insulin Degludec: Multi-Hexamer Formation is the Underlying Basis for This New Generation Ultra-Long Acting Basal Insulin", 2010, vol. 53, No. 1, pp. S388.
R. Cuddihy et al., Diabetologia, "Once-Daily Use of a New Generation Ultra-Long Acting Basal Insulin With a Bolus Boost in Insulin-Naïve People With Type 2 Diabetes: Comparison With Insulin Glargine", 2010, vol. 53, No. 1, pp. S389.
Brange, J et al Diabetic Medicine Neutral Insulin Solutions Physically Stabilized by Addition of ZN2+ 1986 3 6 532-536.
Havelund, S et al. Pharmaceutical Research the Mechanism of Protraction of Insulin . . . 2004 21 8 1498-1504.
Schlichtkrull, J Acta Chemica Scandinavica Insulin Crystals 1956 10 9 1455-1458.
Whittingham.J.L et al. Biochemistry Crystallographic and Solution . . . 2004 43-5987-5995.

\* cited by examiner

US 9,034,818 B2

PHARMACEUTICAL FORMULATIONS COMPRISING AN INSULIN DERIVATIVE

CROSS-REFERENCE TO RELATED APPLICATIONS

This application is a 35 U.S.C. §371 national stage application of International Patent Application PCT/EP2008/057413 (published as WO 2008/152106), filed Jun. 12, 2008, which claimed priority of European Patent Application 07110176.0, filed Jun. 13, 2007; this application further claims priority under 35 U.S.C. §119 of U.S. Provisional Application 60/934,652, filed Jun. 15, 2007.

FIELD OF THE INVENTION

The present invention relates to a soluble pharmaceutical compositions of acylated insulin with a prolonged action profile and high zinc content and a citric acid monohydrate and/or a histidine compound. Further the invention relates to a method for producing a composition with a prolonged action profile and high zinc content and a method for manufacturing the composition for the treatment of diabetes.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Insulin is a 51 amino acid peptide hormone produced in the islets of Langerhans in the pancreas. Its primary function, acting as a monomer, is to facilitate the transport of glucose molecules across the cell membranes of adipose and muscle tissue by binding to and activating a transmembrane receptor.

A distinctive property of insulin is its ability to associate into hexamers, in which form the hormone is protected from chemical and physical degradation during biosynthesis and storage. X-ray crystallographic studies on insulin show that the hexamer consists of three dimers related by a 3-fold axis of rotation. These dimers are closely associated through the interaction of two zinc ions at its core positioned on the 3-fold axis. Two hexamers of insulin may associate into dodecamer insulin complexes, which may associate into even larger complexes, eg. two, three or four dodecamers forming complexes together.

The presence of zinc in insulin formulations increases the tendency of insulin self-association. The more zinc present in the formulation the higher tendency for the insulin to self-associate into hexamers or even larger insulin complexes depending on the conditions. As absorption from the injection site through the capillary wall is negatively correlated with size of the assembly (monomers are absorbed faster than dimers, which in turn are absorbed faster than hexamers etc.) formation of larger insulin complexes will extent the clinical properties of the insulin towards a basal profile.

When human insulin is injected into the subcutis in the form of a high-concentration pharmaceutical formulation it is self associated to primarily hexamers, and here dissociation into monomers is relatively slow. Hexamers and dimers of insulin are slower to penetrate capillary wall than monomers. Therefore when injecting basal insulin it is desired to have as few monomers present as possible.

International patent application WO 99/24071 discloses a method for preventing self-association of insulin into dimers, tetramers and hexamers. The self-association is prevented by the presence of histidine.

International patent application published under number WO 2007/041481 concerns formulation comprising insulin selected from the group consisting of intermediate acting and a long acting insulin with an effective amount of a chelator and an acidifying agent to enhance the rate or amount of uptake by a patient. The chelator may be selected among a number of compounds, e.g. EDTA or citric acid. It is believed that the chelator pulls the zinc away from the insulin, thereby favouring the monomeric form of the insulin over the hexameric form.

It would be desirable to have a soluble formulation of insulin where the insulin is present in the dodecamer form.

SUMMARY OF THE INVENTION

The invention concerns a soluble pharmaceutical formulation comprising an insulin derivative wherein the formulation further comprises
  a) more than 4 zinc atoms per 6 molecules of the insulin derivative,
  b) citric acid monohydrate and/or a histidine compound used in an amount sufficient to increase the tendency of the insulin derivative to self-associate to dodecamers.

In one aspect the invention concerns a shelf-stable soluble pharmaceutical formulation comprising an insulin derivative wherein the formulation further comprises
  a) more than 4 zinc atoms per 6 molecules of insulin derivative
  b) citric acid monohydrate and/or a histidine compound used in an amount sufficient to increase the tendency of the insulin derivative to self-associate to dodecamers.

In one aspect the invention concerns a soluble pharmaceutical formulation comprising an insulin derivative for use as a medicament, wherein the formulation further comprises
  a) more than 4 zinc atoms per 6 molecules of the insulin derivative,
  b) citric acid monohydrate and/or a histidine compound used in an amount sufficient to increase the tendency of the insulin derivative to self-associate into dodecamers.

In one aspect the invention concerns a soluble pharmaceutical formulation comprising an insulin derivative, wherein the formulation further comprises
  a) more than 4 zinc atoms per 6 molecules of the insulin derivative,
  b) citric acid monohydrate and/or a histidine compound used in an amount sufficient to increase the tendency of the insulin derivative to self-associate into dodecamers, and
  c) the insulin derivate has a substituent —W—X—Y—Z attached to the ε-amino group of a Lys residue present in the B chain of the parent insulin, the substituent being of the general formula:

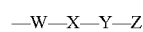

wherein W is:
  an α-amino acid residue having a carboxylic acid group in the side chain which residue forms, with one of its carboxylic acid groups, an amide group together with ε-amino group of a Lys residue present in the B chain of the parent insulin;
  a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to an ε-amino group of a Lys residue present in the B chain of the parent insulin;

X is:
- —$\underline{C}$O—;
- —CH(COOH)$\underline{C}$O—;
- —CO—N(CH$_2$COOH)CH$_2$$\underline{C}$O—;
- —CO—N(CH$_2$COOH)CH$_2$CON(CH$_2$COOH)CH$_2$$\underline{C}$O—;
- —CO—N(CH$_2$CH$_2$COOH)CH$_2$CH$_2$$\underline{C}$O—;
- —CO—N(CH$_2$CH$_2$COOH)CH$_2$CH$_2$CON(CH$_2$CH$_2$COOH)CH$_2$CH$_2$$\underline{C}$O—;
- —CO—NHCH(COOH)(CH$_2$)$_4$NH$\underline{C}$O—;
- —CO—N(CH$_2$CH$_2$COOH)CH$_2$$\underline{C}$O—; or
- —CO—N(CH$_2$COOH)CH$_2$CH$_2$$\underline{C}$O—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
- —(CH$_2$)$_m$— where m is an integer in the range of 6 to 32;
- a divalent hydrocarbon chain comprising 1, 2 or 3 —CH=CH— groups and a number of —CH$_2$— groups sufficient to give a total number of carbon atoms in the chain in the range of 10 to 32; and Z is:
- —COOH;
- —CO-Asp;
- —CO-Glu;
- —CO-Gly;
- —CO-Sar;
- —CH(COOH)$_2$;
- —N(CH$_2$COOH)$_2$;
- —SO$_3$H; or
- —PO$_3$H provided that when W is a covalent bond and X is —CO—, then Z is different from —COOH.

In one aspect the invention concerns the use of citric acid monohydrate and/or a histidine compound in a soluble pharmaceutical formulation comprising an insulin derivative and zinc ions, wherein the citric acid monohydrate and/or the histidine compound is used in an amount sufficient to increase the tendency of said insulin derivative to self-associate to dodecamers.

In one aspect the invention concerns a process for preparing a soluble pharmaceutical formulation comprising
a) Providing an aqueous phase comprising an insulin derivative,
b) Providing more than about 4 zinc ions per 6 molecules of the insulin derivative,
c) Providing citric acid monohydrate and/or a histidine compound to increase the tendency of the insulin derivative to self-associate to dodecamer form,
mixing the aqueous phase, the zinc ions and the citric acid monohydrate and/or a histidine compound to form a soluble pharmaceutical formulation.

In one aspect the invention concerns a process for preparing a shelf-stable soluble pharmaceutical formulation comprising
a) Providing an aqueous phase comprising an insulin derivative
b) Providing more than about 4 zinc ions per 6 molecules of the insulin derivative,
c) Providing citric acid monohydrate and/or a histidine compound to increase the tendency of the insulin derivative to self-associate to dodecamer form,
mixing the aqueous phase, the zinc ions and the citric acid monohydrate and/or a histidine compound to form a soluble pharmaceutical formulation.

DESCRIPTION OF THE DRAWINGS

All figures are generated based on results from size exclusion chromatography of formulations of LysB29Nε-hexadecandioyl-γ-Glu desB30 human insulin.

DEFINITIONS

Figure 1:
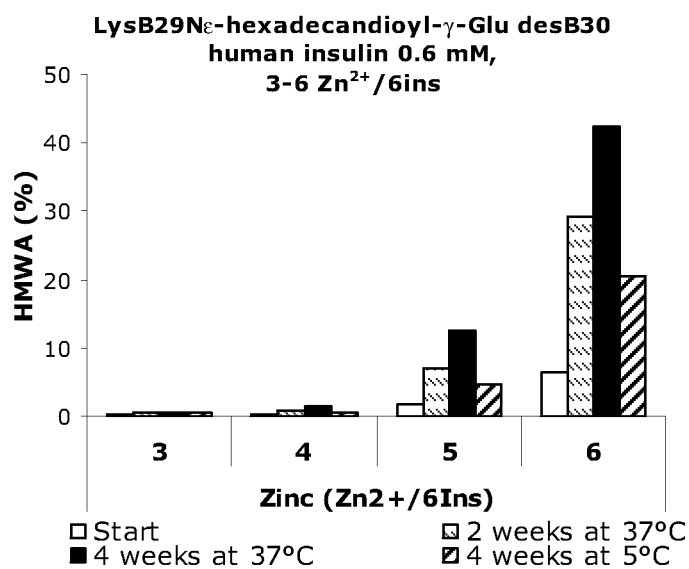
FIG. 1: Fraction of LysB29Nε-hexadecandioyl-γ-Glu desB30 human insulin as HMWA versus zinc concentration and storage time at 5 and 37° C.

The term "dimer" means two insulin molecules which are non-covalently associated.

By use of the term "hexamer" is meant six insulin molecules or three insulin dimers non-covalently associated into an insulin complex. The complex can comprise and will be stabilized by ions such as zinc ions or calcium ions.

By use of the term "dodecamer" is meant 12 insulin molecules non-covalently associated into a complex.

The term "high molecular weight associates" or "hmwa" means a complex that is larger than the insulin dodecamer complex, that is more than 12 insulin molecules non-covalently associated into a complex.

The term "histidine compound" as used herein refers to the amino acid L-histidine and D-histidine, as well as amino acid analogues of L-histidine and D-histidine. Such analogues include, without limitation, dipeptides and tripeptides which contain Histidine, such as but not limited to, His-Gly, Gly-His, Ala-His, 3 methyl-His, 1 methyl-His, carnosine, His-Ser and His-Ala.

The term "citrate compound" as used herein refers to the carboxylic acid citric acid as well as salts hereof. Such salts include, without limitations, sodium salts, potassium salts, zinc salts, calcium salts, magnesium salts and ammonium salts.

The expression "zinc complex forming compound" means citrate compounds or histidine compounds.

By the use of "shelf stable" herein is meant that the majority of the insulin molecules of the pharmaceutical formulation are present as insulin dodecamers and a minor part of the insulin molecules are present as insulin monomers. For example the pharmaceutical formulation stored at 37° C. for 4 weeks comprises at least about 76%, at least about 77%, at least about 78%, at least about 79%, at least about 80% or at least about 85%, at least about 90%, at least about 95%, at least about 98%, at least about 99%, or at least about 99.8% of the insulin molecules in the pharmaceutical formulation are present as dodecamers when measured by SEC with phenol, and the pharmaceutical formulation stored at 37° C. for 4 weeks comprises up to about 5%, up to about 4.5%, up to about 4%, up to about 3.5%, up to about 3.0%, up to about 2.5%, up to about 2.0% or up to about 1.5% of the insulin molecules present as insulin monomers when measure by SEC without phenol.

The expression "SEC with phenol" or "size exclusion chromatography with phenol" means that a TSK-GEL Super SW2000 column is used with isocratic elution with an eluent consisting of 10 mM trishydroxymethylaminomethan, 140 mM NaCl and 2 mM phenol, pH 7.4 at room temperature and 0.3 mL/min. Results are expressed in % dodecamer and % HMWA based on the relative peak area of the individual species.

The expression "SEC without phenol" or "size exclusion chromatography without phenol" means that a Superdex 200 (10/300 GL) column is used with isocratic elution with an eluent consisting of 10 mM trishydroxymethylaminomethan, 140 mM NaCl, pH 7.4 at room temperature and 0.5 mL/min. Results are expressed in % monomer based on the relative peak area of the monomer peak.

With "rapid acting insulin" is meant an insulin which will have an immediately onset of action when injected into subcutis.

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues.

In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

With "desB30 insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B1", "A1" etc. is meant the amino acid residue at position 1 in the B-chain of insulin (counted from the N-terminal end) and the amino acid residue at position 1 in the A-chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin, porcine insulin or bovine insulin with disulfide bridges between CysA7 and CysB7 and between CysA20 and CysB19 and an internal disulfide bridge between CysA6 and CysA11.

By "parent insulin" is meant a naturally occurring insulin such as human insulin or porcine insulin. Alternatively, the parent insulin can be an insulin analogue.

The term "no blunting" as used herein means that when formulated in one formulation both the rapid acting insulin and the acylated insulin has profile of action which is identical or substantially identical with the profile of action, when administering the rapid acting insulin and the acylated insulin in separate formulations.

The following abbreviations have been used in the specification and examples:
HPLC High Performance Liquid Chromatography
SEC size exclusion chromatography
Tris tris(hydroxymethyl)aminomethane
$Zn^{2+}$/6 ins Zinc ions per 6 insulin derivative molecules All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

DESCRIPTION OF THE INVENTION

The invention is based on the recognition that the presence of citric acid monohydrate and/or a histidine compound in a soluble pharmaceutical formulation comprising a relatively high amount of zinc ions increases the tendency of the insulin derivative to self-associate to dodecamers. The majority of the insulin derivative in the soluble pharmaceutical formulation of the invention is therefore present in the dodecamer form resulting in a formulation with a uniform distribution of self-associated insulin derivatives.

The invention concerns a soluble pharmaceutical formulation comprising an insulin derivative wherein the formulation further comprises
  a) more than 4 zinc atoms per 6 molecules of the insulin derivative,
  b) citric acid monohydrate and/or a histidine compound used in an amount sufficient to increase the tendency of the insulin derivative to self-associate to dodecamers.

In one aspect the invention concerns a shelf-stable soluble pharmaceutical formulation comprising an insulin derivative wherein the formulation further comprises
  a) more than 4 zinc atoms per 6 molecules of insulin derivative
  b) citric acid monohydrate and/or a histidine compound used in an amount sufficient to increase the tendency of the insulin derivative to self-associate to dodecamers.

In one aspect the invention concerns a soluble pharmaceutical formulation comprising an insulin derivative for use as a medicament, wherein the formulation further comprises
  a) more than 4 zinc atoms per 6 molecules of the insulin derivative,
  b) citric acid monohydrate and/or a histidine compound used in an amount sufficient to increase the tendency of the insulin derivative to self-associate into dodecamers.

In one aspect the invention concerns a soluble pharmaceutical formulation comprising an insulin derivative, wherein the formulation further comprises
  a) more than 4 zinc atoms per 6 molecules of the insulin derivative,
  b) citric acid monohydrate and/or a histidine compound used in an amount sufficient to increase the tendency of the insulin derivative to self-associate into dodecamers, and
  c) the insulin derivate has a substituent —W—X—Y—Z attached to the $\epsilon$-amino group of a Lys residue present in the B chain of the parent insulin, the substituent being of the general formula:

—W—X—Y—Z wherein W is:
  an $\alpha$-amino acid residue having a carboxylic acid group in the side chain which residue forms, with one of its carboxylic acid groups, an amide group together with $\epsilon$-amino group of a Lys residue present in the B chain of the parent insulin;
  a chain composed of two, three or four $\alpha$-amino acid residues linked together via amide carbonyl bonds, which chain—via an amide bond—is linked to an $\epsilon$-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
  a covalent bond from X to an $\epsilon$-amino group of a Lys residue present in the B chain of the parent insulin;

X is:
  —$\underline{C}$O—;
  —CH(COOH)$\underline{C}$O—;
  —CO—N(CH$_2$COOH)CH$_2$$\underline{C}$O—;
  —CO—N(CH$_2$COOH)CH$_2$CON(CH$_2$COOH)CH$_2$$\underline{C}$O—;
  —CO—N(CH$_2$CH$_2$COOH)CH$_2$CH$_2$$\underline{C}$O—;
  —CO—N(CH$_2$CH$_2$COOH)CH$_2$CH$_2$CON(CH$_2$CH$_2$COOH)CH$_2$CH$_2$$\underline{C}$O—;
  —CO—NHCH(COOH)(CH$_2$)$_4$NH$\underline{C}$O—;
  —CO—N(CH$_2$CH$_2$COOH)CH$_2$$\underline{C}$O—; or
  —CO—N(CH$_2$COOH)CH$_2$CH$_2$$\underline{C}$O—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an $\epsilon$-amino group of a Lys residue present in the B chain of the parent insulin;

Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32; and Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H provided that when W is a covalent bond and X is —CO—, then Z is different from —COOH.

In one aspect the invention concerns the use of citric acid monohydrate and/or a histidine compound in a soluble pharmaceutical formulation comprising an insulin derivative and zinc ions, wherein the citric acid monohydrate and/or a histidine compound is used in an amount sufficient to increase the tendency of said insulin derivative to self-associate to dodecamers.

In one aspect the invention concerns a process for preparing a soluble pharmaceutical formulation comprising
  a) Providing an aqueous phase comprising an insulin derivative,
  b) Providing more than about 4 zinc ions per 6 molecules of the insulin derivative,
  c) Providing citric acid monohydrate and/or a histidine compound to increase the tendency of the insulin derivative to self-associate to dodecamer form,
mixing the aqueous phase, the zinc ions and the citric acid monohydrate or the histidine compound to form a soluble pharmaceutical formulation.

In one aspect the invention concerns a process for preparing a shelf-stable soluble pharmaceutical formulation comprising
  a) Providing an aqueous phase comprising an insulin derivative
  b) Providing more than about 4 zinc ions per 6 molecules of the insulin derivative,
  c) Providing a citric acid monohydrate and/or a histidine compound to increase the tendency of the insulin derivative to self-associate to dodecamer form,
mixing the aqueous phase, the zinc ions and the citric acid monohydrate or the histidine compound to form a soluble pharmaceutical formulation.

The invention are summarized in the following paragraphs:

1. A soluble pharmaceutical formulation comprising an insulin derivative wherein the formulation further comprises
   a) more than 4 zinc atoms per 6 molecules of the insulin derivative,
   b) citric acid monohydrate and/or a histidine compound used in an amount sufficient to increase the tendency of the insulin derivative to self-associate into dodecamers.

2. A shelf-stable soluble pharmaceutical formulation comprising an insulin derivative wherein the formulation further comprises
   a) more than 4 zinc atoms per 6 molecules of insulin derivative
   b) citric acid monohydrate and/or a histidine compound used in an amount sufficient to increase the tendency of the insulin derivative to self-associate into dodecamers.

3. A soluble pharmaceutical formulation comprising an insulin derivative for use as a medicament, wherein the formulation further comprises
   a) more than 4 zinc atoms per 6 molecules of the insulin derivative,
   b) citric acid monohydrate and/or a histidine compound used in an amount sufficient to increase the tendency of the insulin derivative to self-associate into dodecamers.

4. Pharmaceutical formulation according to paragraphs 1, 2 or 3, wherein the formulation comprises more than 4.3 zinc atoms per 6 molecules of the insulin derivative, more than 4.5 zinc atoms per 6 molecules of the insulin derivative, more than 4.7 zinc atoms per 6 molecules of the insulin derivative, more than 4.9 zinc atoms per 6 molecules of the insulin derivative, more than 5 zinc atoms per 6 molecules of the insulin derivative, more than 5.5 zinc atoms per 6 molecules of the insulin derivative, more than 6.5 zinc atoms per 6 molecules of the insulin derivative, more than 7.0 zinc atoms per 6 molecules of the insulin derivative or more than 7.5 zinc atoms per 6 molecules of the insulin derivative.

5. Pharmaceutical formulation according to paragraphs 1-4, wherein the formulation comprises up to 12 zinc ions per 6 molecules of the insulin derivative.

6. Pharmaceutical formulation according to paragraphs 1-5, wherein the pharmaceutical formulation comprises between 4.3 and 12 zinc ions per 6 molecules of the insulin derivative, between 4.5 and 12 zinc ions per 6 molecules of the insulin derivative, between 4.7 and 12 zinc ions per 6 molecules of the insulin derivative, between 4.9 and 12 zinc ions per 6 molecules of the insulin derivative, between 5 and 11.4 zinc atoms per 6 molecules of the insulin derivative, between 5.5 and 10 zinc atoms per 6 molecules of the insulin derivative, between 6 and 10.5 zinc atoms per 6 molecules of the insulin derivative, between 6.5 and 10 zinc atoms per 6 molecules of the insulin derivative or between 7 and 9 zinc atoms per 6 molecules of the insulin derivative.

7. Pharmaceutical formulation according to paragraphs 1-6, wherein the molar ratio between the citric acid monohydrate and/or the histidine compound and zinc ions is from 0.05 to 10.

8. Pharmaceutical formulation according to paragraphs 1-7, wherein the molar ratio between the citric acid monohydrate and/or the histidine compound and zinc ions is from 0.1 to 2, from 0.1 to 1 or from 0.2 to 1.

9. Pharmaceutical formulation according to paragraphs 1-8, wherein the citric acid monohydrate and/or the histidine compound is present in an amount up to 4 mM.

10. Pharmaceutical formulation according to paragraphs 1-9, wherein the citric acid monohydrate and/or the histidine compound is present in an amount from 0.05 mM to 4 mM, from 0.1 mM to 2 mM or from 0.1 to 1.8 mM.

11. Pharmaceutical formulation according to paragraphs 1-10, wherein the citric acid monohydrate and/or the histidine compound is present in an amount up to 1 mM.

12. Pharmaceutical formulation according to paragraphs 1-11, wherein the citric acid monohydrate and/or the histidine compound is present in an amount from 0.05 mM to 0.95 mM.

13. Pharmaceutical formulation according to paragraphs 1-12, wherein the citric acid monohydrate and/or the histidine compound is present in an amount from 0.1 mM to 0.9 mM, from 0.1 mM to 0.8 mM, from 0.1 mM to 0.7 mM, from 0.1 mM to 0.6 mM, from 0.2 mM to 0.9 mM or from 0.2 mM to 0.8 mM.

14. Pharmaceutical formulation according to paragraphs 1-13, wherein at least 76% of the insulin derivative molecules are present as dodecamers when measured by SEC with phenol after storage at 37° C. for 4 weeks.

15. Pharmaceutical formulation according to paragraphs 1-14, wherein at least 77%, at least 78%, at least 79%, at least 80% or at least 85%, at least 90%, at least 95%, at least 98%, at least 99%, or at least 99.8% of the insulin molecules in the pharmaceutical formulation are present as dodecamers when measured by SEC with phenol after storage at 37° C. for 4 weeks.

16. Pharmaceutical formulation according to paragraphs 1-17, wherein up to 5% of the insulin derivative molecules are present as monomers when measured by SEC without phenol after storage at 37° C. for 4 weeks.

17. Pharmaceutical formulation according to paragraphs 1-16, wherein up to 4.5%, up to 4%, up to 3.5%, up to 3.0%, up to 2.5%, up to 2.0% or up to 1.5% of the insulin derivative molecules are present as monomers when measured by SEC without phenol after storage at 37° C. for 4 weeks.

18. Pharmaceutical formulation according to paragraphs 1-17, wherein the histidine compound is dipeptides containing histidine or tripeptides containing histidine, 19. Pharmaceutical formulation to paragraph 18, wherein the histidine compound is L-histidine.

20. Pharmaceutical formulation according to paragraphs 1-19, wherein the insulin derivative is selected from the group consisting of insulin derivatives of human insulin, insulin derivatives of desB30 human insulin, insulin derivatives of insulin analogues, acylated human insulin, acylated desB30 human insulin, acylated insulin analogues, acylated bovine insulin and acylated porcine insulin.

21. Pharmaceutical formulation according to paragraph 1-20, wherein the insulin derivative has a substituent —W—X—Y—Z attached to the ε-amino group of a Lys residue present in the B chain of the parent insulin, the substituent being of the general formula:

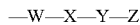

wherein W is:
   an α-amino acid residue having a carboxylic acid group in the side chain which residue forms, with one of its carboxylic acid groups, an amide group together with ε-amino group of a Lys residue present in the B chain of the parent insulin;
   a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or a covalent bond from X to an ε-amino group of a Lys residue present in the B chain of the parent insulin;

X is:
- —CO—;
- —CH(COOH)CO—;
- —CO—N(CH₂COOH)CH₂CO—;
- —CO—N(CH₂COOH)CH₂CON(CH₂COOH)CH₂CO—;
- —CO—N(CH₂CH₂COOH)CH₂CH₂CO—;
- —CO—N(CH₂CH₂COOH)CH₂CH₂CON(CH₂CH₂COOH)CH₂CH₂CO—;
- —CO—NHCH(COOH)(CH₂)₄NHCO—;
- —CO—N(CH₂CH₂COOH)CH₂CO—; or
- —CO—N(CH₂COOH)CH₂CH₂CO—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
- —(CH₂)ₘ— where m is an integer in the range of 6 to 32;
- a divalent hydrocarbon chain comprising 1, 2 or 3 —CH=CH— groups and a number of —CH₂— groups sufficient to give a total number of carbon atoms in the chain in the range of 10 to 32; and Z is:
- —COOH;
- —CO-Asp;
- —CO-Glu;
- —CO-Gly;
- —CO-Sar;
- —CH(COOH)₂;
- —N(CH₂COOH)₂;
- —SO₃H; or
- —PO₃H provided that when W is a covalent bond and X is —CO—, then Z is different from —COOH.

22. Pharmaceutical formulation according to paragraph 21, wherein the formulation comprises an insulin derivative selected from the group consisting of N^εB29—(N^α—(HOOC(CH₂)₁₄CO)-γ-Glu) des(B30) human insulin;

a) more than 4 zinc atoms per 6 molecules of the insulin derivative,
b) a citric acid monohydrate and/or a histidine compound used in an amount sufficient to increase the tendency of the insulin derivative to self-associate into dodecamers, and
c) the insulin derivate has a substituent —W—X—Y—Z attached to the ε-amino group of a Lys residue present in the B chain of the parent insulin, the substituent being of the general formula:

—W—X—Y—Z wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;

X is:
- —CO—;
- —CH(COOH)CO—;
- —CO—N(CH₂COOH)CH₂CO—;
- —CO—N(CH₂COOH)CH₂CON(CH₂COOH)CH₂CO—;
- —CO—N(CH₂CH₂COOH)CH₂CH₂CO—;
- —CO—N(CH₂CH₂COOH)CH₂CH₂CON(CH₂CH₂COOH)CH₂CH₂CO—;
- —CO—NHCH(COOH)(CH₂)₄NHCO—;
- —CO—N(CH₂CH₂COOH)CH₂CO—; or
- —CO—N(CH₂COOH)CH₂CH₂CO—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
- —(CH₂)ₘ— where m is an integer in the range of 6 to 32;
- a divalent hydrocarbon chain comprising 1, 2 or 3 —CH=CH— groups and a number of —CH₂— groups sufficient to give a total number of carbon atoms in the chain in the range of 10 to 32; and Z is:
- —COOH;
- —CO-Asp;
- —CO-Glu;
- —CO-Gly;
- —CO-Sar;
- —CH(COOH)₂;
- —N(CH₂COOH)₂;
- —SO₃H; or
- —PO₃H provided that when W is a covalent bond and X is —CO—, then Z is different from —COOH.

30. Pharmaceutical formulation according to paragraph 29 wherein the formulation comprises more than 4.3 zinc atoms per 6 molecules of the insulin derivative, more than 4.5 zinc atoms per 6 molecules of the insulin derivative, more than 4.7 zinc atoms per 6 molecules of the insulin derivative, more than 4.9 zinc atoms per 6 molecules of the insulin derivative, more than 5 zinc atoms per 6 molecules of the insulin derivative, more than 5.5 zinc atoms per 6 molecules of the insulin derivative, more than 6.5 zinc atoms per 6 molecules of the insulin derivative, more than 7.0 zinc atoms per 6 molecules of the insulin derivative or more than 7.5 zinc atoms per 6 molecules of the insulin derivative.

31. Pharmaceutical formulation according to paragraphs 29-30, wherein the formulation comprises up to 12 zinc ions per 6 molecules of the insulin derivative.

32. Pharmaceutical formulation according to paragraphs 29-31, wherein the pharmaceutical formulation comprises between 4.3 and 12 zinc ions per 6 molecules of the insulin derivative, between 4.5 and 12 zinc ions per 6 molecules of the insulin derivative, between 4.7 and 12 zinc ions per 6 molecules of the insulin derivative, between 4.9 and 12 zinc ions per 6 molecules of the insulin derivative, between 5 and 11.4 zinc atoms per 6 molecules of the insulin derivative, between 5.5 and 10 zinc atoms per 6 molecules of the insulin derivative, between 6 and 10.5 zinc atoms per 6 molecules of the insulin derivative, between 6.5 and 10 zinc atoms per 6 molecules of the insulin derivative or between 7 and 9 zinc atoms per 6 molecules of the insulin derivative.

33. Pharmaceutical formulation according to paragraphs 29-32, wherein the molar ratio between the citric acid monohydrate and/or the histidine compound and zinc ions is from 0.05 to 10.

34. Pharmaceutical formulation according to paragraphs 29-33, wherein the molar ratio between the citric acid monohydrate and/or the histidine compound and zinc ions is from 0.1 to 2, from 0.1 to 1 or from 0.2 to 1.

35. Pharmaceutical formulation according to paragraphs 29-34, wherein the citric acid monohydrate and/or the histidine compound is present in an amount up to 4 mM.

36. Pharmaceutical formulation according to paragraphs 39-35, wherein the citric acid monohydrate and/or the histidine compound is present in an amount from 0.05 mM to 4 mM, from 0.1 mM to 2 mM or from 0.1 to 1.8 mM.

37. Pharmaceutical formulation according to paragraphs 29-36, wherein the citric acid monohydrate and/or the histidine compound is present in an amount up to 1 mM.

38. Pharmaceutical formulation according to paragraphs 29-37, wherein the citric acid monohydrate and/or the histidine compound is present in an amount from 0.05 mM to 0.95 mM.

39. Pharmaceutical formulation according to paragraphs 29-38, wherein the citric acid monohydrate and/or the histidine compound is present in an amount from 0.1 mM to 0.9 mM, from 0.1 mM to 0.8 mM or from 0.1 mM to 0.7 mM, or from 0.1 mM to 0.6 mM or from 0.2 mM to 0.9 mM or from 0.2 mM to 0.8 mM.

40. Pharmaceutical formulation according to paragraphs 29-39, wherein at least 76% of the insulin derivative molecules are present as dodecamers when measured by SEC with phenol after storage at 37° C. for 4 weeks.

41. Pharmaceutical formulation according to paragraphs 29-40, wherein at least 77%, at least 78%, at least 79%, at least 80% or at least 85%, at least 90%, at least 95%, at least 98%, at least 99%, or at least 99.8% of the insulin molecules in the pharmaceutical formulation are present as dodecamers when measured by SEC with phenol after storage at 37° C. for 4 weeks.

42. Pharmaceutical formulation according to paragraphs 29-41, wherein up to 5% of the insulin derivative molecules are present as monomers when measured by SEC without phenol after storage at 37° C. for 4 weeks.

43. Pharmaceutical formulation according to paragraphs 29-42, wherein up to 4.5%, up to 4%, up to 3.5%, up to 3.0%, up to 2.5%, up to 2.0% or up to 1.5% of the insulin derivative molecules are present as monomers when measured by SEC without phenol after storage at 37° C. for 4 weeks.

44. Pharmaceutical formulation according to paragraphs 29-43, wherein the histidine compound is dipeptides containing histidine or tripeptides containing histidine, 45. Pharmaceutical formulation to paragraph 29-44, wherein the histidine compound is L-histidine.

46. Pharmaceutical formulation according to paragraphs 29-45, wherein the formulation comprises an insulin derivative selected from the group consisting of $N^{\epsilon B29}$—($N^{\alpha}$—(HOOC(CH$_2$)$_{14}$CO)-γ-Glu) des(B30) human insulin;

$N^{\epsilon B29}$—($N^{\alpha}$—(HOOC(CH$_2$)$_{15}$CO)-γ-Glu) des(B30) human insulin;

$N^{\epsilon B29}$—($N^{\alpha}$—(HOOC(CH$_2$)$_{16}$CO)-γ-Glu) des(B30) human insulin;

$N^{\epsilon B29}$—($N^{\alpha}$—(HOOC(CH$_2$)$_{17}$CO)-γ-Glu) des(B30) human insulin;

$N^{\epsilon B29}$—($N^{\alpha}$—(HOOC(CH$_2$)$_{18}$CO)-γ-Glu) des(B30) human insulin;

$N^{\epsilon B29}$—($N^{\alpha}$—(HOOC(CH$_2$)$_{16}$CO)-γ-Glu-N-(γ-Glu)) des(B30) human insulin;

$N^{\epsilon B29}$—($N^{\alpha}$-(Asp-OC(CH$_2$)$_{16}$CO)-γ-Glu) des(B30) human insulin;

$N^{\epsilon B29}$—($N^{\alpha}$-(Glu-OC(CH$_2$)$_{14}$CO)-γ-Glu) des(B30) human insulin;

$N^{\epsilon B29}$—($N^{\alpha}$-(Glu-OC(CH$_2$)$_{14}$CO—) des(B30) human insulin;

$N^{\epsilon B29}$—($N^{\alpha}$-(Asp-OC(CH$_2$)$_{16}$CO—) des(B30) human insulin;

$N^{\epsilon B29}$—($N^{\alpha}$—(HOOC(CH$_2$)$_{16}$CO)-α-Glu-N-(β-Asp)) des(B30) human insulin;

$N^{\epsilon B29}$—($N^{\alpha}$-(Gly-OC(CH$_2$)$_{13}$CO)-γ-Glu) des(B30) human insulin;

$N^{\epsilon B29}$—($N^{\alpha}$-(Sar-OC(CH$_2$)$_{13}$CO)-γ-Glu) des(B30) human insulin;

$N^{\epsilon B29}$—($N^{\alpha}$—(HOOC(CH$_2$)$_{13}$CO)-γ-Glu) des(B30) human insulin;

$N^{\epsilon B29}$—($N^{\alpha}$—(HOOC(CH$_2$)$_{13}$CO)-β-Asp) des(B30) human insulin;

$N^{\epsilon B29}$—($N^{\alpha}$—(HOOC(CH$_2$)$_{13}$CO)-α-Glu) des(B30) human insulin;

$N^{\epsilon B29}$—($N^{\alpha}$—(HOOC(CH$_2$)$_{16}$CO)-γ-Glu) des(B30) human insulin;

$N^{\epsilon B29}$-hexadecandioyl-γ-Glu desB30 human insulin; and $N^{\epsilon B29}$—($N^{\alpha}$—(HOOC(CH$_2$)$_{14}$CO)-β-D-Asp) des(B30) human insulin 47. Pharmaceutical formulation according to paragraphs 29-46, wherein the pharmaceutical formulation further comprises a rapid acting insulin.

48. Pharmaceutical formulation according to paragraph 47, wherein the rapid acting insulin is AspB28 human insulin, LysB3GluB29 human insulin and/or LysB28ProB29 human insulin.

49. Pharmaceutical formulation according to paragraphs 29-48, wherein the pharmaceutical formulation further comprises one or more excipients selected from the group consisting of preservatives, buffers, stabilizers, bulking agents, carriers, isotonic agent and surfactants.

50. Pharmaceutical formulation according to paragraphs 29-49, wherein the pH of the formulation is in the range of 6.5 to 8.5.

51. Pharmaceutical formulation according to paragraphs 29-50, wherein the pH of the formulation is in the range from 7.0 to 8.0 or from 7.4 to 7.6.

52. Use of a citric acid monohydrate and/or a histidine compound in a soluble pharmaceutical formulation comprising an insulin derivative and zinc ions, wherein the citric acid monohydrate and/or the histidine compound is used in an amount sufficient to increase the tendency of said insulin derivative to self-associate into dodecamers.

53. Use according to paragraph 52, wherein the pharmaceutical formulation comprises more than 4 zinc ions per 6 molecules of the insulin derivative.

54. Use according to paragraphs 52-53, wherein the formulation comprises more than 4.3 zinc atoms per 6 molecules of the insulin derivative, more than 4.5 zinc atoms per 6 molecules of the insulin derivative, more than 4.7 zinc atoms per 6 molecules of the insulin derivative, more than 4.9 zinc atoms per 6 molecules of the insulin derivative, more than 5 zinc atoms per 6 molecules of the insulin derivative, more than 5.5 zinc atoms per 6 molecules of the insulin derivative, more than 6.5 zinc atoms per 6 molecules of the insulin derivative, more than 7.0 zinc atoms per 6 molecules of the insulin derivative or more than 7.5 zinc atoms per 6 molecules of the insulin derivative.

55. Use according to paragraphs 52-54, wherein the formulation comprises up to 12 zinc ions per 6 molecules of the insulin derivative.

56. Use according to paragraphs 52-55, wherein the pharmaceutical formulation comprises between 4.3 and 12 zinc ions per 6 molecules of the insulin derivative, between 4.5 and 12 zinc ions per 6 molecules of the insulin derivative, between 4.7 and 12 zinc ions per 6 molecules of the insulin derivative, between 4.9 and 12 zinc ions per 6 molecules of the insulin derivative, between 5 and 11.4 zinc atoms per 6 molecules of the insulin derivative, between 5.5 and 10 zinc atoms per 6 molecules of the insulin derivative, between 6 and 10.5 zinc atoms per 6 molecules of the insulin derivative, between 6.5 and 10 zinc atoms per 6 molecules of the insulin derivative or between 7 and 9 zinc atoms per 6 molecules of the insulin derivative.

57. Use according to paragraphs 52-56, wherein the molar ratio between the citric acid monohydrate and/or the histidine compound and zinc ions is from 0.05 to 10.

58. Use according to paragraphs 52-57, wherein the molar ratio between the citric acid monohydrate and/or the histidine compound and zinc ions is from 0.1 to 2, from 0.1 to 1 or from 0.2 to 1.

59. Use according to paragraphs 52-58, wherein the citric acid monohydrate and/or the histidine compound is present in an amount up to 4 mM.

60. Use according to paragraphs 52-59, wherein the citric acid monohydrate and/or the histidine compound is present in an amount from 0.05 mM to 4 mM, from 0.1 mM to 2 mM or from 0.1 to 1.8 mM.

61. Use according to paragraphs 52-60, wherein the citric acid monohydrate and/or the histidine compound is present in an amount up to 1 mM.

62. Use according to paragraphs 52-61, wherein the citric acid monohydrate and/or the histidine compound is present in an amount from 0.05 mM to 0.95 mM.

63. Use according to paragraphs 52-62, wherein the citric acid monohydrate and/or the histidine compound is present in an amount from 0.1 mM to 0.9 mM, from 0.1 mM to 0.8 mM or from 0.1 mM to 0.7 mM, or from 0.1 mM to 0.6 mM or from 0.2 mM to 0.9 mM or from 0.2 mM to 0.8 mM.

64. Use according to paragraphs 52-63, wherein at least 76% of the insulin derivative molecules are present as dodecamers when measured by SEC with phenol after storage at 37° C. for 4 weeks.

65. Use according to paragraphs 52-64, wherein at least 77%, at least 78%, at least 79%, at least 80% or at least 85%, at least 90%, at least 95%, at least 98%, at least 99%, or at least 99.8% of the insulin molecules in the pharmaceutical formulation are present as dodecamers when measured by SEC with phenol after storage at 37° C. for 4 weeks.

66. Use according to paragraphs 52-65, wherein up to 5% of the insulin derivative molecules are present as monomers when measured by SEC without phenol after storage at 37° C. for 4 weeks.

67. Use according to paragraphs 52-66, wherein up to 4.5%, up to 4%, up to 3.5%, up to 3.0%, up to 2.5%, up to 2.0% or up to 1.5% of the insulin derivative molecules are present as monomers when measured by SEC without phenol after storage at 37° C. for 4 weeks.

68. Use according to paragraphs 52-67, wherein the histidine compound is dipeptides containing histidine or tripeptides containing histidine, 69. Use to paragraph 52-68, wherein the histidine compound is L-histidine.

70. Use according to paragraphs 52-69, wherein the insulin derivative has a substituent —W—X—Y—Z attached to the ε-amino group of a Lys residue present in the B chain of the parent insulin, the substituent being of the general formula:

—W—X—Y—Z wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;

X is:
—C̲O—;
—CH(COOH)C̲O—;
—CO—N(CH$_2$COOH)CH$_2$C̲O—;
—CO—N(CH$_2$COOH)CH$_2$CON(CH$_2$COOH)CH$_2$C̲O—;
—CO—N(CH$_2$CH$_2$COOH)CH$_2$CH$_2$C̲O—;
—CO—N(CH$_2$CH$_2$COOH)CH$_2$CH$_2$CON(CH$_2$CH$_2$COOH)CH$_2$CH$_2$C̲O—;
—CO—NHCH(COOH)(CH$_2$)$_4$NHC̲O—;
—CO—N(CH$_2$CH$_2$COOH)CH$_2$C̲O—; or
—CO—N(CH$_2$COOH)CH$_2$CH$_2$C̲O—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H provided that when W is a covalent bond and X is —CO—, then Z is different from —COOH.

71. Use according to paragraphs 52-70, wherein the insulin derivative selected from the group consisting of
N$^{εB29}$—(N$^α$—(HOOC(CH$_2$)$_{14}$CO)-γ-Glu) des(B30) human insulin;

$N^{\epsilon B29}$—($N^{\alpha}$—(HOOC(CH$_2$)$_{15}$CO)-γ-Glu) des(B30) human insulin;
$N^{\epsilon B29}$—($N^{\alpha}$—(HOOC(CH$_2$)$_{16}$CO)-γ-Glu) des(B30) human insulin;
$N^{\epsilon B29}$—($N^{\alpha}$—(HOOC(CH$_2$)$_{17}$CO)-γ-Glu) des(B30) human insulin;
$N^{\epsilon B29}$—($N^{\alpha}$—(HOOC(CH$_2$)$_{18}$CO)-γ-Glu) des(B30) human insulin;
$N^{\epsilon B29}$—($N^{\alpha}$—(HOOC(CH$_2$)$_{16}$CO)-γ-Glu-N-(γ-Glu)) des(B30) human insulin;
$N^{\epsilon B29}$—($N^{\alpha}$-(Asp-OC(CH$_2$)$_{16}$CO)-γ-Glu) des(B30) human insulin;
$N^{\epsilon B29}$—($N^{\alpha}$-(Glu-OC(CH$_2$)$_{14}$CO)-γ-Glu) des(B30) human insulin;
$N^{\epsilon B29}$—($N^{\alpha}$-(Glu-OC(CH$_2$)$_{14}$CO—) des(B30) human insulin;
$N^{\epsilon B29}$—($N^{\alpha}$-(Asp-OC(CH$_2$)$_{16}$CO—) des(B30) human insulin;
$N^{\epsilon B29}$—($N^{\alpha}$—(HOOC(CH$_2$)$_{16}$CO)-α-Glu-N-(β-Asp)) des(B30) human insulin;
$N^{\epsilon B29}$—($N^{\alpha}$-(Gly-OC(CH$_2$)$_{13}$CO)-γ-Glu) des(B30) human insulin;
$N^{\epsilon B29}$—($N^{\alpha}$-(Sar-OC(CH$_2$)$_{13}$CO)-γ-Glu) des(B30) human insulin;
$N^{\epsilon B29}$—($N^{\alpha}$—(HOOC(CH$_2$)$_{13}$CO)-γ-Glu) des(B30) human insulin;
$N^{\epsilon B29}$—($N^{\alpha}$—(HOOC(CH$_2$)$_{13}$CO)-β-Asp) des(B30) human insulin;
$N^{\epsilon B29}$—($N^{\alpha}$—(HOOC(CH$_2$)$_{13}$CO)-α-Glu) des(B30) human insulin;
$N^{\epsilon B29}$—($N^{\alpha}$—(HOOC(CH$_2$)$_{16}$CO)-γ-D-Glu) des(B30) human insulin;
$N^{\epsilon B29}$-hexadecandioyl-γ-Glu desB30 human insulin; and
$N^{\epsilon B29}$—($N^{\alpha}$—(HOOC(CH$_2$)$_{14}$CO)-β-D-Asp) des(B30) human insulin 72. Use according to paragraphs 52-69, wherein the insulin derivative is $N^{\epsilon B}$29-ω-carboxy-pentadecanoyl-γ-L-glutamylamide desB30 human insulin or $N^{\epsilon B}$29-ω-carboxy-pentadecanoyl-γ-amino-butanoyl desB30 human insulin.

73. Use according to paragraphs 52-72, wherein the pharmaceutical formulation further comprises a rapid acting insulin.

74. Use according to paragraph 73, wherein the rapid acting insulin is AspB28 human insulin, LysB3GluB29 human insulin and/or LysB28ProB29 human insulin.

75. Use according to paragraphs 52-74, wherein the pharmaceutical formulation further comprises one or more excipients selected from the group consisting of preservatives, buffers, stabilizers, bulking agents, carriers, isotonic agent and surfactants.

76. A process for preparing a soluble pharmaceutical formulation comprising
  a) Providing an aqueous phase comprising an insulin derivative,
  b) Providing more than 4 zinc ions per 6 molecules of the insulin derivative,
  c) Providing citric acid monohydrate and/or a histidine compound to increase the tendency of the insulin derivative to self-associate to dodecamer form,
mixing the aqueous phase, the zinc ions and the citric acid monohydrate and/or the histidine compound to form a soluble pharmaceutical formulation.

77. A process for preparing a shelf-stable soluble pharmaceutical formulation comprising
  a) Providing an aqueous phase comprising an insulin derivative
  b) Providing more than 4 zinc ions per 6 molecules of the insulin derivative,
  c) Providing a citric acid monohydrate and/or a histidine compound to increase the tendency of the insulin derivative to self-associate to dodecamer form,
mixing the aqueous phase, the zinc ions and the citric acid monohydrate and/or the histidine compound to form a soluble pharmaceutical formulation.

78. Process according to paragraphs 76 or 77, wherein the formulation comprises more than 4.3 zinc atoms per 6 molecules of the insulin derivative, more than 4.5 zinc atoms per 6 molecules of the insulin derivative, more than 4.7 zinc atoms per 6 molecules of the insulin derivative, more than 4.9 zinc atoms per 6 molecules of the insulin derivative, more than 5 zinc atoms per 6 molecules of the insulin derivative, more than 5.5 zinc atoms per 6 molecules of the insulin derivative, more than 6.5 zinc atoms per 6 molecules of the insulin derivative, more than 7.0 zinc atoms per 6 molecules of the insulin derivative or more than 7.5 zinc atoms per 6 molecules of the insulin derivative.

79. Process according to paragraphs 76-78, wherein the formulation comprises up to 12 zinc ions per 6 molecules of the insulin derivative.

80. Process according to paragraphs 76-79, wherein the pharmaceutical formulation comprises between 4.3 and 12 zinc ions per 6 molecules of the insulin derivative, between 4.5 and 12 zinc ions per 6 molecules of the insulin derivative, between 4.7 and 12 zinc ions per 6 molecules of the insulin derivative, between 4.9 and 12 zinc ions per 6 molecules of the insulin derivative, between 5 and 11.4 zinc atoms per 6 molecules of the insulin derivative, between 5.5 and 10 zinc atoms per 6 molecules of the insulin derivative, between 6 and 10.5 zinc atoms per 6 molecules of the insulin derivative, between 6.5 and 10 zinc atoms per 6 molecules of the insulin derivative or between 7 and 9 zinc atoms per 6 molecules of the insulin derivative.

81. Process according to paragraphs 76-80, wherein the zinc atoms are mixed in the pharmaceutical formulation in two or more than two steps.

82. Process according to paragraphs 76-80, wherein the pharmaceutical formulation is provided by mixing zinc atoms in the aqueous phase in three, four, five or six steps.

83. Process according to paragraphs 76-81, wherein the pharmaceutical formulation is provided by mixing zinc atoms in the aqueous phase before mixing in a preservative.

84. Process according to paragraphs 76-83, wherein the pharmaceutical formulation is provided by mixing zinc atoms in the pharmaceutical formulation after mixing in a preservative.

85. Process according to paragraphs 76-84, the pharmaceutical formulation is provided by mixing in zinc atoms in at least two steps, wherein at least one first step comprises mixing in zinc atoms in the pharmaceutical formulation before mixing in a preservative and at least one second step comprises mixing in zinc atoms after mixing in the preservative.

86. Process according to paragraphs 76-85, wherein the preservative is phenol and/or m-cresol.

87. Process according to paragraphs 76-86, wherein the molar ratio between the citric acid monohydrate an/or the histidine compound and zinc ions is from 0.05 to 10.

88. Process according to paragraphs 76-87, wherein the molar ratio between the citric acid monohydrate and/or the histidine compound and zinc ions is from 0.1 to 2, from 0.1 to 1 or from 0.2 to 1.

89. Process according to paragraphs 76-88, wherein the citric acid monohydrate and/or the histidine compound is present in an amount up to 4 mM.

90. Process according to paragraphs 76-89, wherein the citric acid monohydrate and/or the histidine compound is present in an amount from 0.05 mM to 4 mM, from 0.1 mM to 2 mM or from 0.1 to 1.8 mM.

91. Process according to paragraphs 76-90, wherein the citric acid monohydrate and/or the histidine compound is present in an amount up to 1 mM.

92. Process according to paragraphs 76-91, wherein the citric acid monohydrate and/or the histidine compound is present in an amount from 0.05 mM to 0.95 mM.

93. Process according to paragraphs 76-92, wherein the citric acid monohydrate and/or the histidine compound is present in an amount from 0.1 mM to 0.9 mM, from 0.1 mM to 0.8 mM or from 0.1 mM to 0.7 mM, or from 0.1 mM to 0.6 mM or from 0.2 mM to 0.9 mM or from 0.2 mM to 0.8 mM.

94. Process according to paragraphs 76-93, wherein at least 76% of the insulin derivative molecules are present as dodecamers when measured by SEC with phenol after storage at 37° C. for 4 weeks.

95. Process according to paragraphs 76-94, wherein at least 77%, at least 78%, at least 79%, at least 80% or at least 85%, at least 90%, at least 95%, at least 98%, at least 99%, or at least 99.8% of the insulin molecules in the pharmaceutical formulation are present as dodecamers when measured by SEC with phenol after storage at 37° C. for 4 weeks.

96. Process according to paragraphs 76-95, wherein up to 5% of the insulin derivative molecules are present as monomers when measured by SEC without phenol after storage at 37° C. for 4 weeks.

97. Process according to paragraphs 76-96, wherein up to 4.5%, up to 4%, up to 3.5%, up to 3.0%, up to 2.5%, up to 2.0% or up to 1.5% of the insulin derivative molecules are present as monomers when measured by SEC without phenol after storage at 37° C. for 4 weeks.

98. Process according to paragraphs 76-97, wherein the histidine compound is dipeptides containing histidine or tripeptides containing histidine, 99. Process according to paragraph 98, wherein the histidine compound is L-histidine.

100. Process according to paragraphs 76-99, wherein the insulin derivative is selected from the group consisting of insulin derivatives of human insulin, insulin derivatives of desB30 human insulin, insulin derivatives of insulin analogues, acylated human insulin, acylated desB30 human insulin, acylated insulin analogues, acylated bovine insulin and acylated porcine insulin.

101. Process according to paragraph 76-100, wherein the insulin derivative has a substituent —W—X—Y—Z attached to the ε-amino group of a Lys residue present in the B chain of the parent insulin, the substituent being of the general formula:

—W—X—Y—Z wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;

X is:
—$\underline{C}$O—;
—CH(COOH)$\underline{C}$O—;
—CO—N(CH$_2$COOH)CH$_2$$\underline{C}$O—;
—CO—N(CH$_2$COOH)CH$_2$CON(CH$_2$COOH)CH$_2$$\underline{C}$O—;
—CO—N(CH$_2$CH$_2$COOH)CH$_2$CH$_2$$\underline{C}$O—;
—CO—N(CH$_2$CH$_2$COOH)CH$_2$CH$_2$CON(CH$_2$CH$_2$COOH)CH$_2$CH$_2$$\underline{C}$O—;
—CO—NHCH(COOH)(CH$_2$)$_4$NH$\underline{C}$O—;
—CO—N(CH$_2$CH$_2$COOH)CH$_2$$\underline{C}$O—; or
—CO—N(CH$_2$COOH)CH$_2$CH$_2$$\underline{C}$O—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 10 to 32; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H provided that when W is a covalent bond and X is —CO—, then Z is different from —COOH.

102. Process according to paragraphs 76-101, wherein the insulin derivative is selected from the group consisting of
N$^{εB29}$—(N$^α$—(HOOC(CH$_2$)$_{14}$CO)-γ-Glu) des(B30) human insulin;
N$^{εB29}$—(N$^α$—(HOOC(CH$_2$)$_{15}$CO)-γ-Glu) des(B30) human insulin;
N$^{εB29}$—(N$^α$—(HOOC(CH$_2$)$_{16}$CO)-γ-Glu) des(B30) human insulin;
N$^{εB29}$—(N$^α$—(HOOC(CH$_2$)$_{17}$CO)-γ-Glu) des(B30) human insulin;
N$^{εB29}$—(N$^α$—(HOOC(CH$_2$)$_{18}$CO)-γ-Glu) des(B30) human insulin;
N$^{εB29}$—(N$^α$—(HOOC(CH$_2$)$_{16}$CO)-γ-Glu-N-(γ-Glu)) des(B30) human insulin;
N$^{εB29}$—(N$^α$-(Asp-OC(CH$_2$)$_{16}$CO)-γ-Glu) des(B30) human insulin;
N$^{εB29}$—(N$^α$-(Glu-OC(CH$_2$)$_{14}$CO)-γ-Glu) des(B30) human insulin;
N$^{εB29}$—(N$^α$-(Glu-OC(CH$_2$)$_{14}$CO—) des(B30) human insulin;
N$^{εB29}$—(N$^α$-(Asp-OC(CH$_2$)$_{16}$CO—) des(B30) human insulin;

$N^{\epsilon B29}$—($N^\alpha$—(HOOC(CH$_2$)$_{16}$CO)-α-Glu-N-(β-Asp)) des(B30) human insulin;

$N^{\epsilon B29}$—($N^\alpha$-(Gly-OC(CH$_2$)$_{13}$CO)-γ-Glu) des(B30) human insulin;

$N^{\epsilon B29}$—($N^\alpha$-(Sar-OC(CH$_2$)$_{13}$CO)-γ-Glu) des(B30) human insulin;

$N^{\epsilon B29}$—($N^\alpha$—(HOOC(CH$_2$)$_{13}$CO)-γ-Glu) des(B30) human insulin;

$N^{\epsilon B29}$—($N^\alpha$—(HOOC(CH$_2$)$_{13}$CO)-β-Asp) des(B30) human insulin;

$N^{\epsilon B29}$—($N^\alpha$—(HOOC(CH$_2$)$_{13}$CO)-α-Glu) des(B30) human insulin;

$N^{\epsilon B29}$—($N^\alpha$—(HOOC(CH$_2$)$_{16}$CO)-γ-D-Glu) des(B30) human insulin;

$N^{\epsilon B29}$-hexadecandioyl-γ-Glu desB30 human insulin; and $N^{\epsilon B29}$—($N^\alpha$—(HOOC(CH$_2$)$_{14}$CO)-β-D-Asp) des(B30) human insulin 103. Process according to paragraphs 76-100, wherein the insulin derivative is $N^{\epsilon B}$29-ω-carboxy-pentadecanoyl-γ-L-glutamylamide desB30 human insulin or $N^{\epsilon B29}$-ω-carboxy-pentadecanoyl-γ-amino-butanoyl desB30 human insulin.

104. Process according to paragraphs 76-103, wherein the pharmaceutical formulation further comprises a rapid acting insulin.

105. Process according to paragraph 104, wherein the rapid acting insulin is AspB28 human insulin, LysB3GluB29 human insulin and/or LysB28ProB29 human insulin.

106. Process according to paragraphs 76-105, wherein the pharmaceutical formulation further comprises one or more excipients selected from the group consisting of preservatives, buffers, stabilizers, bulking agents, carriers, isotonic agent and surfactants.

107. Use of a soluble pharmaceutical formulation comprising a therapeutically effective amount of an insulin derivative and more than 4 zinc atoms per six molecules of the insulin derivative for the treatment of type 1 diabetes, type 2 diabetes and other states that cause hyperglycaemia in patients in need of such a treatment.

108. Method for treating type 1, type 2 diabetes and other states that cause hyperglycaemia in patients in need of such a treatment by the use of a soluble pharmaceutical formulation comprising an insulin derivative, more than 4 zinc atoms per 6 molecules of the insulin derivative and a citric acid monohydrate and/or a histidine compound.

109. Method according to paragraph 108, wherein the histidine compound is dipeptides containing histidine or tripeptides containing histidine, 110. Method to paragraph 108-109, wherein the histidine compound is L-histidine.

111. A soluble pharmaceutical formulation as described in the examples.

The insulin derivative according to the invention and the rapid acting insulin analogue can be mixed in a ratio from 90/10%, 70/30%, 50/50%, 30/70% or 10/90%.

In one aspect, the invention relates to a pharmaceutical formulation comprising an insulin derivative according to the invention which is soluble at physiological pH values.

In one aspect, the invention relates to a pharmaceutical formulation comprising an insulin derivative according to the invention which is soluble at pH values in the interval from 6.5 to 8.5.

In one aspect, the invention relates to a pharmaceutical formulation which is a solution containing from 120 nmol/ml to 2400 nmol/ml, from 400 nmol/ml to 2400 nmol/ml, from 400 nmol/ml to 1200 nmol/ml, from 600 nmol/ml to 2400 nmol/ml, or from 600 nmol/ml to 1200 nmol/ml of an insulin derivative or of a mixture of the insulin derivative with a rapid acting insulin analogue.

When preparing the insulin derivatives to be used in the pharmaceutical formulation according to the invention, the starting product for the substitution, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture. Reference is made to international patent application WO 2005/012347.

Pharmaceutical Compositions

The pharmaceutical formulations of this invention can, for example, be administered subcutaneously, parentally, orally, nasal, buccal pulmonary.

For subcutaneous administration, the pharmaceutical formulations are formulated analogously with the pharmaceutical formulation of known insulin. Furthermore, for subcutaneous administration, the compounds of the formula are administered analogously with the administration of known insulin and, generally, the physicians are familiar with this procedure.

According to the invention, a pharmaceutical formulation of this invention may be delivered by inhalation to achieve rapid absorption thereof. Administration by inhalation can result in pharmacokinetics comparable to subcutaneous administration of insulin. Inhalation of a pharmaceutical formulation of this invention leads to a rapid rise in the level of circulating insulin followed by a rapid fall in blood glucose levels. Different inhalation devices typically provide similar pharmacokinetics when similar particle sizes and similar levels of lung deposition are compared.

According to the invention, pharmaceutical formulations of this invention may be delivered by any of a variety of inhalation devices known in the art for administration of a therapeutic agent by inhalation. These devices include metered dose inhalers, nebulizers, dry powder generators, sprayers, and the like. Preferably, an acylated insulin composition of this invention is delivered by a dry powder inhaler or a sprayer. There are a several desirable features of an inhalation device for administering an acylated insulin composition of this invention. For example, delivery by the inhalation device is advantageously reliable, reproducible, and accurate. The inhalation device should deliver small particles, for example, less than about 10 μm, for example about 1-5 μm, for good respirability. Some specific examples of commercially available inhalation devices suitable for the practice of this invention are Turbohaler™ (Astra), Rotahaler® (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), the C-Haler© (Microdrug), the E-Flex© (Microdrug) or the like.

As those skilled in the art will recognize, pharmaceutical formulations of this invention, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of insulin conjugate in the aerosol. For example, shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and preferably into the lower airways or alveoli. Preferably, pharmaceutical formulations of this invention is formulated so that at least about 10% of the insulin conjugate delivered is deposited in the lung, preferably about 10 to about 20%, or more. It is known that the maximum efficiency of pulmonary deposition for mouth breathing humans is obtained with particle sizes of about 2 µm to about 3 µm. When particle sizes are above about 5 µm pulmonary deposition decreases substantially. Particle sizes below about 1 µm cause pulmonary deposition to decrease, and it becomes difficult to deliver particles with sufficient mass to be therapeutically effective. Thus, particles delivered by inhalation have a particle size preferably less than about 10 µm, more preferably in the range of about 1 µm to about 5 µm. The formulation of insulin is selected to yield the desired particle size in the chosen inhalation device.

Advantageously for administration as a dry powder, an acylated insulin composition of this invention is prepared in a particulate form with a particle size of less than about 10 µm, preferably about 1 to about 5 µm. The preferred particle size is effective for delivery to the alveoli of the patient's lung. Preferably, the dry powder is largely composed of particles produced so that a majority of the particles have a size in the desired range. Advantageously, at least about 50% of the dry powder is made of particles having a diameter less than about 10 µm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Pharmaceutical formulations of this invention for administration from a dry powder inhaler typically include a finely divided dry powder containing insulin, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, anti-oxidants or buffers), to provide taste to the formulation, or the like. Advantageously, the additive does not adversely affect the patient's airways. The insulin can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulation of a protein such as insulin analogue protein can also be included in the formulation.

A spray including the pharmaceutical formulation of this invention can be produced by forcing a solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 µm, preferably in the range of about 1 µm to about 5 µm.

Pharmaceutical formulations of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, preferably, zinc. The formulation can also include an excipient or agent for stabilization of the insulin, such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The pharmaceutical formulation can also include a surfactant, which can reduce or prevent surface-induced aggregation of the insulin conjugate caused by atomization of the solution in forming an aerosol. Various conventional surfactants can be employed, such as polyoxyethylene fatty acid esters and alcohols, and polyoxyethylene sorbitol fatty acid esters. Amounts will generally range between about 0.001 and about 4% by weight of the formulation.

The pharmaceutical compositions according to the present invention may be administered parenterally to patients in need of such a treatment. Parenteral administration may be performed by subcutaneous, intramuscular or intravenous injection by means of a syringe, optionally a pen-like syringe or another convenient dosing equipment. Alternatively, parenteral administration can be performed by means of an infusion pump.

Injectable compositions of the pharmaceutical formulation can be prepared using the conventional techniques of the pharmaceutical industry which involve dissolving and mixing the ingredients as appropriate to give the desired end product. Thus, according to one procedure, the insulin is dissolved in an amount of water which is somewhat less than the final volume of the composition to be prepared. An isotonic agent, a preservative or a mixture of preservatives, zinc as acetate or chloride or a mixture thereof, and a buffer can be added as required, furthermore a surfactant might be added and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

The buffer may be selected from the group consisting of sodium acetate, sodium carbonate, glycine, lysine, arginine, sodium dihydrogen phosphate, disodium hydrogen phosphate, sodium phosphate, ADA (N-[2-acetamido]-2-iminodiacetic acid), ACES (N-[2-acetamido]-2-aminoethanesulfonic acid), BES (N,N-bis[2-hydroxyethyl]-2-aminoethanesulfonic acid), bicine (N,N-bis-[2-hydroxyethyl]glycine), BIS-TRIS (bis[2-hydroxyethyl]iminotris[hydroxymethyl]-methane), DIPSO (3[N,N-bis(2-hydroxyethyl]amin]-2-hydroxypropanesulfonic acid), ethylenediamine dihydrochloride, glycylglycine, HEPES (N-[2-hydroxyethyl]piperazine-N'-[2-ethanesulfonic acid]), HEPPSO (N-[2-hydroxyethyl]piperazine-N'-[2-hydroxypropanesulfonic acid]), imidazole, MOBS (4-[N-morpholino]butanesulfonic acid), MOPS (3-[N-morpholino]propanesulfonic acid), PIPES (piperazine-N,N'-bis[2-ethanesulfonic acid]), TAPSO (3-[N-tris(hydroxymethyl)methylamino]-2-hydroxypropanesulfonic acid, THAM (tris[hydroxymethyl]-aminomethan), TES (N-tris[hydroxymethyl]methyl-2-aminoethanesulfonic acid, tricine (N-tris[hydroxymethyl]methylglycine), adipic acid, aspartic acid, glutaric acid, malic acid, malonic acid, succinic acid, and/or salts thereof and/or mixtures thereof.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)propane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy*, 19$^{th}$ edition, 1995.

In a further aspect of the invention the formulation further comprises an isotonic agent which may be selected from the group consisting of a salt (e.g. sodium chloride), a sugar or sugar alcohol, an amino acid (e.g. I-glycine, arginine, lysine, isoleucine, aspartic acid, tryptophan, threonine), 1,2-propanediol (propyleneglycol), 1,3-propanediol, 1,3-butanediol)polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one aspect the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid composition and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy*, 19$^{th}$ edition, 1995.

In a further aspect of the invention the formulation comprises a surfactant to prevent fibrillation especially when mixing the insulin derivative with a rapid acting insulin as insulin aspart. Various conventional surfactants can be employed, such as polyoxyethylene fatty acid esters and alcohols, and polyoxyethylene sorbitol fatty acid esters. Amounts will generally range between about 0.001 and about 0.1% by weight of the formulation.

In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)—derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives—(e.g. sodium tauro-dihydrofusidate etc.), long-chain fatty acids and salts thereof C6-C12 (eg. oleic acid and caprylic acid), acylcarnitines and derivatives, N$^\alpha$-acylated derivatives of lysine, arginine or histidine, or side-chain acylated derivatives of lysine or arginine, N$^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

Typical isotonic agents are sodium chloride, mannitol, dimethyl sulfone, 1,2 propandiol, and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid), tris-hydroxymethyl-aminomethan, ethylenediamine dihydrochloride, and sodium phosphate.

The pharmaceutical compositions according to the present invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific acylated insulin or mixture of the acylated insulin with a rapid acting insulin employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

The present invention is further illustrated by the following examples which, however, are not to be construed as limiting the scope of protection.

The following paragraphs summarizes the invention:

1a. Pharmaceutical formulation comprising an insulin derivative wherein the formulation further comprises
  c) more than 4 zinc atoms per 6 molecules of the insulin derivative,
  d) a zinc complex forming compound used in an amount sufficient to increase the tendency of the insulin derivative to self-associate into dodecamers.

2a. A shelf-stable pharmaceutical formulation comprising an insulin derivative wherein the formulation further comprises
  c) more than 4 zinc atoms per 6 molecules of insulin derivative
  d) a zinc complex forming compound used in an amount sufficient to increase the tendency of the insulin derivative to self-associate into dodecamers.

3a. Pharmaceutical formulation comprising an insulin derivative for the treatment of type 1 diabetes, type 2 diabetes and other states that cause hyperglycaemia in patients in need of such a treatment, wherein the formulation further comprises
  c) more than 4 zinc atoms per 6 molecules of the insulin derivative,
  d) a zinc complex forming compound used in an amount sufficient to increase the tendency of the insulin derivative to self-associate into dodecamers.

4a. Pharmaceutical formulation according to paragraphs 1, 2 or 3, wherein the formulation comprises more than about 4.3 zinc atoms per 6 molecules of the insulin derivative, more than about 4.5 zinc atoms per 6 molecules of the insulin derivative, more than about 4.7 zinc atoms per 6 molecules of the insulin derivative, more than about 4.9 zinc atoms per 6 molecules of the insulin derivative, more than about 5 zinc atoms per 6 molecules of the insulin derivative, more than about 5.5 zinc atoms per 6 molecules of the insulin derivative, more than about 6.5 zinc atoms per 6 molecules of the insulin derivative, more than about 7.0 zinc atoms per 6 molecules of the insulin derivative or more than about 7.5 zinc atoms per 6 molecules of the insulin derivative.

5a. Pharmaceutical formulation according to paragraphs 1-4, wherein the formulation comprises up to about 12 zinc ions per 6 molecules of the insulin derivative.

6a. Pharmaceutical formulation according to paragraphs 1-5, wherein the pharmaceutical formulation comprises between about 4.3 and about 12 zinc ions per 6 molecules of the insulin derivative, between about 4.5 and about 12 zinc ions per 6 molecules of the insulin derivative, between about 4.7 and about 12 zinc ions per 6 molecules of the insulin derivative, between about 4.9 and about 12 zinc ions per 6 molecules of the insulin derivative, between about 5 and about 11.4 zinc atoms per 6 molecules of the insulin derivative, between about 5.5 and about 10 zinc atoms per 6 molecules of the insulin derivative, between about 6 and about 10.5 zinc atoms per 6 molecules of the insulin derivative, between about 6.5 and about 10 zinc atoms per 6 molecules of the insulin derivative or between about 7 and about 9 zinc atoms per 6 molecules of the insulin derivative.

7a. Pharmaceutical formulation according to paragraphs 1-6, wherein the molar ratio between the zinc complex forming compound and zinc ions is from about 0.05 to about 10.

8a. Pharmaceutical formulation according to paragraphs 1-7, wherein the molar ratio between the zinc complex forming compound and zinc ions is from about 0.1 to about 2, from about 0.1 to about 1 or from about 0.2 to about 1.

9a. Pharmaceutical formulation according to paragraphs 1-8, wherein the zinc complex forming compound is present in an amount up to about 4 mM.

10a. Pharmaceutical formulation according to paragraphs 1-9, wherein the zinc complex forming compound is present in an amount from about 0.05 mM to about 4 mM, from about 0.1 mM to about 2 mM or from about 0.1 to about 1.8 mM.

11a. Pharmaceutical formulation according to paragraphs 1-10, wherein the zinc complex forming compound is present in an amount up to about 1 mM.

12a. Pharmaceutical formulation according to paragraphs 1-11, wherein the zinc complex forming compound is present in an amount from about 0.05 mM to about 0.95 mM.

13a. Pharmaceutical formulation according to paragraphs 1-12, wherein the zinc complex forming compound is present in an amount from about 0.1 mM to about 0.9 mM, from about 0.1 mM to about 0.8 mM, from about 0.1 mM to about 0.7 mM, from about 0.1 mM to about 0.6 mM, from about 0.2 mM to about 0.9 mM or from about 0.2 mM to about 0.8 mM.

14a. Pharmaceutical formulation according to paragraphs 1-13, wherein at least about 76% of the insulin derivative molecules are present as dodecamers when measured by SEC with phenol after storage at 37° C. for 4 weeks.

15a. Pharmaceutical formulation according to paragraphs 1-14, wherein at least about 77%, at least about 78%, at least about 79%, at least about 80% or at least about 85%, at least about 90%, at least about 95%, at least about 98%, at least about 99%, or at least about 99.8% of the insulin molecules in the pharmaceutical formulation are present as dodecamers when measured by SEC with phenol after storage at 37° C. for 4 weeks.

16a. Pharmaceutical formulation according to paragraphs 1-17, wherein up to about 5% of the insulin derivative molecules are present as monomers when measured by SEC without phenol after storage at 37° C. for 4 weeks.

17a. Pharmaceutical formulation according to paragraphs 1-16, wherein up to about 4.5%, up to about 4%, up to about 3.5%, up to about 3.0%, up to about 2.5%, up to about 2.0% or up to about 1.5% of the insulin derivative molecules are present as monomers when measured by SEC without phenol after storage at 37° C. for 4 weeks.

18a. Pharmaceutical formulation according to paragraphs 1-17, wherein zinc complex forming compound is citrate compounds and/or histidine compounds.

19a. Pharmaceutical formulation according to paragraph 18, wherein the citrate compound is citric acid monohydrate.

20a. Pharmaceutical formulation according to paragraphs 1-19, wherein the histidine compound is dipeptides containing histidine or tripeptides containing histidine, 21a. Pharmaceutical formulation to paragraph 20, wherein the zinc complex forming compound is L-histidine.

22a. Pharmaceutical formulation according to paragraphs 1-21, wherein the insulin derivative is selected from the group consisting of insulin derivatives of human insulin, insulin derivatives of desB30 human insulin, insulin derivatives of insulin analogues, acylated human insulin, acylated desB30 human insulin, acylated insulin analogues, acylated bovine insulin and acylated porcine insulin.

23a. Pharmaceutical formulation according to paragraph 1-22, wherein the insulin derivative has a substituent —W—X—Y—Z attached to the ε-amino group of a Lys residue present in the B chain of the parent insulin, the substituent being of the general formula:

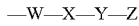

wherein W is:
  an α-amino acid residue having a carboxylic acid group in the side chain which residue forms, with one of its carboxylic acid groups, an amide group together with ε-amino group of a Lys residue present in the B chain of the parent insulin;
  a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
  a covalent bond from X to an ε-amino group of a Lys residue present in the B chain of the parent insulin;

X is:
  —CO—;
  —CH(COOH)CO—;
  —CO—N(CH$_2$COOH)CH$_2$CO—;
  —CO—N(CH$_2$COOH)CH$_2$CON(CH$_2$COOH)CH$_2$CO—;
  —CO—N(CH$_2$CH$_2$COOH)CH$_2$CH$_2$CO—;
  —CO—N(CH$_2$CH$_2$COOH)CH$_2$CH$_2$CON(CH$_2$CH$_2$COOH)CH$_2$CH$_2$CO—;
  —CO—NHCH(COOH)(CH$_2$)$_4$NHCO—;
  —CO—N(CH$_2$CH$_2$COOH)CH$_2$CO—; or
  —CO—N(CH$_2$COOH)CH$_2$CH$_2$CO—.

that
a) when W is an amino acid residue or a chain of amino acid residues, via a bond from the underscored carbon forms an amide bond with an amino group in W, or b) when W is a covalent bond, via a bond from the underscored carbonyl carbon forms an amide bond with an ε-amino group of a Lys residue present in the B chain of the parent insulin;

Y is:
  —(CH$_2$)$_m$— where m is an integer in the range of 6 to 32;
  a divalent hydrocarbon chain comprising 1, 2 or 3 —CH═CH— groups and a number of —CH$_2$— groups sufficient to give a total number of carbon atoms in the chain in the range of 10 to 32; and Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H provided that when W is a covalent bond and X is —CO—, then Z is different from —COOH.

24a. Pharmaceutical formulation according to paragraph 23, wherein the formulation comprises an insulin derivative selected from the group consisting of
  N$^{εB29}$—(N$^α$—(HOOC(CH$_2$)$_{14}$CO)-γ-Glu) des(B30) human insulin;
  N$^{εB29}$—(N$^α$—(HOOC(CH$_2$)$_{15}$CO)-γ-Glu) des(B30) human insulin;
  N$^{εB29}$—(N$^α$—(HOOC(CH$_2$)$_{16}$CO)-γ-Glu) des(B30) human insulin;
  N$^{εB29}$—(N$^α$—(HOOC(CH$_2$)$_{17}$CO)-γ-Glu) des(B30) human insulin;
  N$^{εB29}$—(N$^α$—(HOOC(CH$_2$)$_{18}$CO)-γ-Glu) des(B30) human insulin;
  N$^{εB29}$—(N$^α$—(HOOC(CH$_2$)$_{16}$CO)-γ-Glu-N-(γ-Glu)) des(B30) human insulin;
  N$^{εB29}$—(N$^α$-(Asp-OC(CH$_2$)$_{16}$CO)-γ-Glu) des(B30) human insulin;
  N$^{εB29}$—(N$^α$-(Glu-OC(CH$_2$)$_{14}$CO)-γ-Glu) des(B30) human insulin;
  N$^{εB29}$—(N$^{60}$-(Glu-OC(CH$_2$)$_{14}$CO—) des(B30) human insulin;
  N$^{εB29}$—(N$^α$-(Asp-OC(CH$_2$)$_{16}$CO—) des(B30) human insulin;
  N$^{εB29}$—(N$^α$—(HOOC(CH$_2$)$_{16}$CO)-α-Glu-N-(β-Asp)) des(B30) human insulin;
  N$^{εB29}$—(N$^α$-(Gly-OC(CH$_2$)$_{13}$CO)-γ-Glu) des(B30) human insulin;
  N$^{εB29}$—(N$^α$-(Sar-OC(CH$_2$)$_{13}$CO)-γ-Glu) des(B30) human insulin;
  N$^{εB29}$—(N$^α$—(HOOC(CH$_2$)$_{13}$CO)-γ-Glu) des(B30) human insulin;
  N$^{εB29}$—(N$^α$—(HOOC(CH$_2$)$_{13}$CO)-β-Asp) des(B30) human insulin;
  N$^{εB29}$—(N$^α$—(HOOC(CH$_2$)$_{13}$CO)-α-Glu) des(B30) human insulin;
  N$^{εB29}$—(N$^α$—(HOOC(CH$_2$)$_{16}$CO)-γ-D-Glu) des(B30) human insulin;
  N$^{εB29}$-hexadecandioyl-γ-Glu desB30 human insulin; and
  N$^{εB29}$—(N$^α$—(HOOC(CH$_2$)$_{14}$CO)-β-D-Asp) des(B30) human insulin 25a. Pharmaceutical formulation according to paragraphs 1-22, wherein the insulin derivative is N$^{εB29}$-ω-carboxy-pentadecanoyl-γ-L-glutamylamide desB30 human insulin or N$^{εB29}$-ω-carboxy-pentadecanoyl-γ-amino-butanoyl desB30 human insulin.

26a. Pharmaceutical formulation according to paragraphs 1-25, wherein the pharmaceutical formulation further comprises a rapid acting insulin.

27a. Pharmaceutical formulation according to paragraph 26, wherein the rapid acting insulin is AspB28 human insulin, LysB3GluB29 human insulin and/or LysB28ProB29 human insulin.

28a. Pharmaceutical formulation according to paragraphs 1-27, wherein the pharmaceutical formulation further comprises one or more excipients selected from the group consisting of preservatives, buffers, stabilizers, bulking agents, carriers, isotonic agent and surfactants.

29a. Pharmaceutical formulation according to paragraphs 1-28, wherein the pH of the formulation is in the range of about 6.5 to 8.5.

30a. Pharmaceutical formulation according to paragraphs 1-29, wherein the pH of the formulation is in the range from about 7.0 to about 8.0 or from about 7.4 to about 7.6.

31a. Pharmaceutical formulation comprising an insulin derivative, wherein the formulation further comprises
  d) more than 4 zinc atoms per 6 molecules of the insulin derivative,
  e) a zinc complex forming compound used in an amount sufficient to increase the tendency of the insulin derivative to self-associate into dodecamers, and
  f) the insulin derivate has a substituent —W—X—Y—Z attached to the ε-amino group of a Lys residue present in the B chain of the parent insulin, the substituent being of the general formula:

—W—X—Y—Z wherein W is:
  an α-amino acid residue having a carboxylic acid group in the side chain which residue forms, with one of its carboxylic acid groups, an amide group together with ε-amino group of a Lys residue present in the B chain of the parent insulin;
  a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
  a covalent bond from X to an ε-amino group of a Lys residue present in the B chain of the parent insulin;
X is:
  —$\underline{C}$O—;
  —CH(COOH)$\underline{C}$O—;
  —CO—N(CH$_2$COOH)CH$_2$$\underline{C}$O—;
  —CO—N(CH$_2$COOH)CH$_2$CON(CH$_2$COOH)CH$_2$$\underline{C}$O—;
  —CO—N(CH$_2$CH$_2$COOH)CH$_2$CH$_2$$\underline{C}$O—;
  —CO—N(CH$_2$CH$_2$COOH)CH$_2$CH$_2$CON(CH$_2$CH$_2$COOH)CH$_2$CH$_2$$\underline{C}$O—;
  —CO—NHCH(COOH)(CH$_2$)$_4$NH$\underline{C}$O—;
  —CO—N(CH$_2$CH$_2$COOH)CH$_2$$\underline{C}$O—; or
  —CO—N(CH$_2$COOH)CH$_2$CH$_2$$\underline{C}$O—.
that
a) when W is an amino acid residue or a chain of amino acid residues, via a bond from the underscored carbon forms an amide bond with an amino group in W, or b) when W is a covalent bond, via a bond from the underscored carbonyl carbon forms an amide bond with an ε-amino group of a Lys residue present in the B chain of the parent insulin;
Y is:
  —(CH$_2$)$_m$— where m is an integer in the range of 6 to 32;
  a divalent hydrocarbon chain comprising 1, 2 or 3 —CH=CH— groups and a number of —CH$_2$— groups sufficient to give a total number of carbon atoms in the chain in the range of 10 to 32; and
Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H; or
  —PO$_3$H
provided that when W is a covalent bond and X is —CO—, then Z is different from —COOH.

32a. Pharmaceutical formulation according to paragraph 31, wherein the formulation comprises more than about 4.3 zinc atoms per 6 molecules of the insulin derivative, more than about 4.5 zinc atoms per 6 molecules of the insulin derivative, more than about 4.7 zinc atoms per 6 molecules of the insulin derivative, more than about 4.9 zinc atoms per 6 molecules of the insulin derivative, more than about 5 zinc atoms per 6 molecules of the insulin derivative, more than about 5.5 zinc atoms per 6 molecules of the insulin derivative, more than about 6.5 zinc atoms per 6 molecules of the insulin derivative, more than about 7.0 zinc atoms per 6 molecules of the insulin derivative or more than about 7.5 zinc atoms per 6 molecules of the insulin derivative.

33a. Pharmaceutical formulation according to paragraphs 31-32, wherein the formulation comprises up to about 12 zinc ions per 6 molecules of the insulin derivative.

34a. Pharmaceutical formulation according to paragraphs 31-33, wherein the pharmaceutical formulation comprises between about 4.3 and about 12 zinc ions per 6 molecules of the insulin derivative, between about 4.5 and about 12 zinc ions per 6 molecules of the insulin derivative, between about 4.7 and about 12 zinc ions per 6 molecules of the insulin derivative, between about 4.9 and about 12 zinc ions per 6 molecules of the insulin derivative, between about 5 and about 11.4 zinc atoms per 6 molecules of the insulin derivative, between about 5.5 and about 10 zinc atoms per 6 molecules of the insulin derivative, between about 6 and about 10.5 zinc atoms per 6 molecules of the insulin derivative, between about 6.5 and about 10 zinc atoms per 6 molecules of the insulin derivative or between about 7 and about 9 zinc atoms per 6 molecules of the insulin derivative.

35a. Pharmaceutical formulation according to paragraphs 31-34, wherein the molar ratio between the zinc complex forming compound and zinc ions is from about 0.05 to about 10.

36a. Pharmaceutical formulation according to paragraphs 31-35, wherein the molar ratio between the zinc complex forming compound and zinc ions is from about 0.1 to about 2, from about 0.1 to about 1 or from about 0.2 to about 1.

37a. Pharmaceutical formulation according to paragraphs 31-36, wherein the zinc complex forming compound is present in an amount up to about 4 mM.

38a. Pharmaceutical formulation according to paragraphs 31-37, wherein the zinc complex forming compound is present in an amount from about 0.05 mM to about 4 mM, from about 0.1 mM to about 2 mM or from about 0.1 to about 1.8 mM.

39a. Pharmaceutical formulation according to paragraphs 31-38, wherein the zinc complex forming compound is present in an amount up to about 1 mM.

40a. Pharmaceutical formulation according to paragraphs 31-39, wherein the zinc complex forming compound is present in an amount from about 0.05 mM to about 0.95 mM.

41a. Pharmaceutical formulation according to paragraphs 31-40, wherein the zinc complex forming compound is present in an amount from about 0.1 mM to about 0.9 mM, from about 0.1 mM to about 0.8 mM or from about 0.1 mM to about 0.7 mM, or from about 0.1 mM to about 0.6 mM or from about 0.2 mM to about 0.9 mM or from about 0.2 mM to about 0.8 mM.

42a. Pharmaceutical formulation according to paragraphs 31-41, wherein at least about 76% of the insulin derivative molecules are present as dodecamers when measured by SEC with phenol after storage at 37° C. for 4 weeks.

43a. Pharmaceutical formulation according to paragraphs 31-42, wherein at least about 77%, at least about 78%, at least about 79%, at least about 80% or at least about 85%, at least about 90%, at least about 95%, at least about 98%, at least about 99%, or at least about 99.8% of the insulin molecules in the pharmaceutical formulation are present as dodecamers when measured by SEC with phenol after storage at 37° C. for 4 weeks.

44a. Pharmaceutical formulation according to paragraphs 31-43, wherein up to about 5% of the insulin derivative molecules are present as monomers when measured by SEC without phenol after storage at 37° C. for 4 weeks.

45a. Pharmaceutical formulation according to paragraphs 31-44, wherein up to about 4.5%, up to about 4%, up to about 3.5%, up to about 3.0%, up to about 2.5%, up to about 2.0% or up to about 1.5% of the insulin derivative molecules are present as monomers when measured by SEC without phenol after storage at 37° C. for 4 weeks.

46a. Pharmaceutical formulation according to paragraphs 31-45, wherein zinc complex forming compound is citrate compounds and/or histidine compounds.

47a. Pharmaceutical formulation according to paragraph 31-46, wherein the citrate compound is citric acid monohydrate.

48a. Pharmaceutical formulation according to paragraphs 31-47, wherein the histidine compound is dipeptides containing histidine or tripeptides containing histidine, 49a. Pharmaceutical formulation to paragraph 31-48, wherein the zinc complex forming compound is L-histidine.

50a. Pharmaceutical formulation according to paragraphs 31-49, wherein the formulation comprises an insulin derivative selected from the group consisting of $N^{\epsilon B29}$—($N^{\alpha}$—(HOOC(CH$_2$)$_{14}$CO)-γ-Glu) des(B30) human insulin;

$N^{\epsilon B29}$—($N^{\alpha}$—(HOOC(CH$_2$)$_{15}$CO)-γ-Glu) des(B30) human insulin;

$N^{\epsilon B29}$—($N^{\alpha}$—(HOOC(CH$_2$)$_{16}$CO)-γ-Glu) des(B30) human insulin;

$N^{\epsilon B29}$—($N^{\alpha}$—(HOOC(CH$_2$)$_{17}$CO)-γ-Glu) des(B30) human insulin;

$N^{\epsilon B29}$—($N^{\alpha}$—(HOOC(CH$_2$)$_{18}$CO)-γ-Glu) des(B30) human insulin;

$N^{\epsilon B29}$—($N^{\alpha}$—(HOOC(CH$_2$)$_{16}$CO)-γ-Glu-N-(γ-Glu)) des(B30) human insulin;

$N^{\epsilon B29}$—($N^{\alpha}$-(Asp-OC(CH$_2$)$_{16}$CO)-γ-Glu) des(B30) human insulin;

$N^{\epsilon B29}$—($N^{\alpha}$-(Glu-OC(CH$_2$)$_{14}$CO)-γ-Glu) des(B30) human insulin;

$N^{\epsilon B29}$—($N^{\alpha}$-(Glu-OC(CH$_2$)$_{14}$CO—) des(B30) human insulin;

$N^{\epsilon B29}$—($N^{\alpha}$-(Asp-OC(CH$_2$)$_{16}$CO—) des(B30) human insulin;

$N^{\epsilon B29}$—($N^{\alpha}$—(HOOC(CH$_2$)$_{16}$CO)-α-Glu-N-(β-Asp)) des(B30) human insulin;

$N^{\epsilon B29}$—($N^{\alpha}$-(Gly-OC(CH$_2$)$_{13}$CO)-γ-Glu) des(B30) human insulin;

$N^{\epsilon B29}$—($N^{\alpha}$-(Sar-OC(CH$_2$)$_{13}$CO)-γ-Glu) des(B30) human insulin;

$N^{\epsilon B29}$—($N^{\alpha}$—(HOOC(CH$_2$)$_{13}$CO)-γ-Glu) des(B30) human insulin;

$N^{\epsilon B29}$—($N^{\alpha}$—(HOOC(CH$_2$)$_{13}$CO)-β-Asp) des(B30) human insulin;

$N^{\epsilon B29}$—($N^{\alpha}$—(HOOC(CH$_2$)$_{13}$CO)-α-Glu) des(B30) human insulin;

$N^{\epsilon B29}$—($N^{\alpha}$—(HOOC(CH$_2$)$_{16}$CO)-γ-D-Glu) des(B30) human insulin;

$N^{\epsilon B29}$-hexadecandioyl-γ-Glu desB30 human insulin; and $N^{\epsilon B29}$—($N^{\alpha}$—(HOOC(CH$_2$)$_{14}$CO)-β-D-Asp) des(B30) human insulin 51a. Pharmaceutical formulation according to paragraphs 31-50, wherein the pharmaceutical formulation further comprises a rapid acting insulin.

52a. Pharmaceutical formulation according to paragraph 51, wherein the rapid acting insulin is AspB28 human insulin, LysB3GluB29 human insulin and/or LysB28ProB29 human insulin.

53a. Pharmaceutical formulation according to paragraphs 31-52, wherein the pharmaceutical formulation further comprises one or more excipients selected from the group consisting of preservatives, buffers, stabilizers, bulking agents, carriers, isotonic agent and surfactants.

54a. Pharmaceutical formulation according to paragraphs 31-53, wherein the pH of the formulation is in the range of about 6.5 to 8.5.

55a. Pharmaceutical formulation according to paragraphs 31-54, wherein the pH of the formulation is in the range from about 7.0 to about 8.0 or from about 7.4 to about 7.6.

56a. Use of zinc complex forming compound in a pharmaceutical formulation comprising an insulin derivative and zinc ions, wherein the zinc complex forming compound is used in an amount sufficient to increase the tendency of said insulin derivative to self-associate into dodecamers.

57a. Use according to paragraph 56, wherein the pharmaceutical formulation comprises more than 4 zinc ions per 6 molecules of the insulin derivative.

58a. Use according to paragraphs 56-57, wherein the formulation comprises more than about 4.3 zinc atoms per 6 molecules of the insulin derivative, more than about 4.5 zinc atoms per 6 molecules of the insulin derivative, more than about 4.7 zinc atoms per 6 molecules of the insulin derivative, more than about 4.9 zinc atoms per 6 molecules of the insulin derivative, more than about 5 zinc atoms per 6 molecules of the insulin derivative, more than about 5.5 zinc atoms per 6 molecules of the insulin derivative, more than about 6.5 zinc atoms per 6 molecules of the insulin derivative, more than about 7.0 zinc atoms per 6 molecules of the insulin derivative or more than about 7.5 zinc atoms per 6 molecules of the insulin derivative.

59a. Use according to paragraphs 56-58, wherein the formulation comprises up to about 12 zinc ions per 6 molecules of the insulin derivative.

60a. Use according to paragraphs 56-59, wherein the pharmaceutical formulation comprises between about 4.3 and about 12 zinc ions per 6 molecules of the insulin derivative, between about 4.5 and about 12 zinc ions per 6 molecules of the insulin derivative, between about 4.7 and about 12 zinc ions per 6 molecules of the insulin derivative, between about 4.9 and about 12 zinc ions per 6 molecules of the insulin derivative, between about 5 and about 11.4 zinc atoms per 6 molecules of the insulin derivative, between about 5.5 and about 10 zinc atoms per 6 molecules of the insulin derivative, between about 6 and about 10.5 zinc atoms per 6 molecules of the insulin derivative, between about 6.5 and about 10 zinc atoms per 6 molecules of the insulin derivative or between about 7 and about 9 zinc atoms per 6 molecules of the insulin derivative.

61a. Use according to paragraphs 56-60, wherein the molar ratio between the zinc complex forming compound and zinc ions is from about 0.05 to about 10.

62a. Use according to paragraphs 56-61, wherein the molar ratio between the zinc complex forming compound and zinc ions is from about 0.1 to about 2, from about 0.1 to about 1 or from about 0.2 to about 1.

63a. Use according to paragraphs 56-62, wherein the zinc complex forming compound is present in an amount up to about 4 mM.

64a. Use according to paragraphs 56-63, wherein the zinc complex forming compound is present in an amount from about 0.05 mM to about 4 mM, from about 0.1 mM to about 2 mM or from about 0.1 to about 1.8 mM.

65a. Use according to paragraphs 56-64, wherein the zinc complex forming compound is present in an amount up to about 1 mM.

66a. Use according to paragraphs 56-65, wherein the zinc complex forming compound is present in an amount from about 0.05 mM to about 0.95 mM.

67a. Use according to paragraphs 56-66, wherein the zinc complex forming compound is present in an amount from about 0.1 mM to about 0.9 mM, from about 0.1 mM to about 0.8 mM or from about 0.1 mM to about 0.7 mM, or from about 0.1 mM to about 0.6 mM or from about 0.2 mM to about 0.9 mM or from about 0.2 mM to about 0.8 mM.

68a. Use according to paragraphs 56-67, wherein at least about 76% of the insulin derivative molecules are present as dodecamers when measured by SEC with phenol after storage at 37° C. for 4 weeks.

69a. Use according to paragraphs 56-68, wherein at least about 77%, at least about 78%, at least about 79%, at least about 80% or at least about 85%, at least about 90%, at least about 95%, at least about 98%, at least about 99%, or at least about 99.8% of the insulin molecules in the pharmaceutical formulation are present as dodecamers when measured by SEC with phenol after storage at 37° C. for 4 weeks.

70a. Use according to paragraphs 56-69, wherein up to about 5% of the insulin derivative molecules are present as monomers when measured by SEC without phenol after storage at 37° C. for 4 weeks.

71a. Use according to paragraphs 56-70, wherein up to about 4.5%, up to about 4%, up to about 3.5%, up to about 3.0%, up to about 2.5%, up to about 2.0% or up to about 1.5% of the insulin derivative molecules are present as monomers when measured by SEC without phenol after storage at 37° C. for 4 weeks.

72a. Use according to paragraphs 56-71, wherein zinc complex forming compound is citrate compounds and/or histidine compounds.

73a. Use according to paragraph 56-72, wherein the citrate compound is citric acid monohydrate.

74a. Use according to paragraphs 56-73, wherein the histidine compound is dipeptides containing histidine or tripeptides containing histidine, 75a. Use to paragraph 56-73, wherein the zinc complex forming compound is L-histidine.

76a. Use according to paragraphs 56-75, wherein the insulin derivative has a substituent —W—X—Y—Z attached to the ε-amino group of a Lys residue present in the B chain of the parent insulin, the substituent being of the general formula:

—W—X—Y—Z wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;

X is:
—CO—;
—CH(COOH)CO—;
—CO—N(CH$_2$COOH)CH$_2$CO—;
—CO—N(CH$_2$COOH)CH$_2$CON(CH$_2$COOH)CH$_2$CO—;
—CO—N(CH$_2$CH$_2$COOH)CH$_2$CH$_2$CO—;
—CO—N(CH$_2$CH$_2$COOH)CH$_2$CH$_2$CON(CH$_2$CH$_2$COOH)CH$_2$CH$_2$CO—;
—CO—NHCH(COOH)(CH$_2$)$_4$NHCO—;
—CO—N(CH$_2$CH$_2$COOH)CH$_2$CO—; or
—CO—N(CH$_2$COOH)CH$_2$CH$_2$CO—.

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 —CH=CH— groups and a number of —CH$_2$— groups sufficient to give a total number of carbon atoms in the chain in the range of 10 to 32; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H provided that when W is a covalent bond and X is —CO—, then Z is different from —COOH.

77a. Use according to paragraphs 56-76, wherein the insulin derivative selected from the group consisting of $N^{\epsilon B29}$—($N^{\alpha}$—(HOOC(CH$_2$)$_{14}$CO)-γ-Glu) des(B30) human insulin;

$N^{\epsilon B29}$—($N^{\alpha}$—(HOOC(CH$_2$)$_{15}$CO)-γ-Glu) des(B30) human insulin;

$N^{\epsilon B29}$—($N^{\alpha}$—(HOOC(CH$_2$)$_{16}$CO)-γ-Glu) des(B30) human insulin;

$N^{\epsilon B29}$—($N^{\alpha}$—(HOOC(CH$_2$)$_{17}$CO)-γ-Glu) des(B30) human insulin;

$N^{\epsilon B29}$—($N^{\alpha}$—(HOOC(CH$_2$)$_{18}$CO)-γ-Glu) des(B30) human insulin;

$N^{\epsilon B29}$—($N^{\alpha}$—(HOOC(CH$_2$)$_{16}$CO)-γ-Glu-N-(γ-Glu)) des(B30) human insulin;

$N^{\epsilon B29}$—($N^{\alpha}$-(Asp-OC(CH$_2$)$_{16}$CO)-γ-Glu) des(B30) human insulin;

$N^{\epsilon B29}$—($N^{\alpha}$-(Glu-OC(CH$_2$)$_{14}$CO)-γ-Glu) des(B30) human insulin;

$N^{\epsilon B29}$—($N^{\alpha}$-(Glu-OC(CH$_2$)$_{14}$CO—) des(B30) human insulin;

$N^{\epsilon B29}$—($N^{\alpha}$-(Asp-OC(CH$_2$)$_{16}$CO—) des(B30) human insulin;

$N^{\epsilon B29}$—($N^{\alpha}$—(HOOC(CH$_2$)$_{16}$CO)-α-Glu-N-(β-Asp)) des(B30) human insulin;

$N^{\epsilon B29}$—($N^{\alpha}$-(Gly-OC(CH$_2$)$_{13}$CO)-γ-Glu) des(B30) human insulin;

$N^{\epsilon B29}$—($N^{\alpha}$-(Sar-OC(CH$_2$)$_{13}$CO)-γ-Glu) des(B30) human insulin;

$N^{\epsilon B29}$—($N^{\alpha}$—(HOOC(CH$_2$)$_{13}$CO)-γ-Glu) des(B30) human insulin;

$N^{\epsilon B29}$—($N^{\alpha}$—(HOOC(CH$_2$)$_{13}$CO)-β-Asp) des(B30) human insulin;

$N^{\epsilon B29}$—($N^{\alpha}$—(HOOC(CH$_2$)$_{13}$CO)-α-Glu) des(B30) human insulin;

$N^{\epsilon B29}$—($N^{\alpha}$—(HOOC(CH$_2$)$_{16}$CO)-γ-D-Glu) des(B30) human insulin;

$N^{\epsilon B29}$-hexadecandioyl-γ-Glu desB30 human insulin; and $N^{\epsilon B29}$—($N^{\alpha}$—(HOOC(CH$_2$)$_{14}$CO)-β-D-Asp) des(B30) human insulin 78a. Use according to paragraphs 56-75, wherein the insulin derivative is $N^{\epsilon B29}$-ω-carboxy-pentadecanoyl-γ-L-glutamylamide desB30 human insulin or $N^{\epsilon B29}$-ω-carboxy-pentadecanoyl-γ-amino-butanoyl desB30 human insulin.

79a. Use according to paragraphs 56-78, wherein the pharmaceutical formulation further comprises a rapid acting insulin.

80a. Use according to paragraph 79, wherein the rapid acting insulin is AspB28 human insulin, LysB3GluB29 human insulin and/or LysB28ProB29 human insulin.

81a. Use according to paragraphs 56-80, wherein the pharmaceutical formulation further comprises one or more excipients selected from the group consisting of preservatives, buffers, stabilizers, bulking agents, carriers, isotonic agent and surfactants.

82a. A process for preparing a pharmaceutical formulation comprising
  d) Providing an aqueous phase comprising an insulin derivative,
  e) Providing more than about 4 zinc ions per 6 molecules of the insulin derivative,
  f) Providing a zinc complex forming compound to increase the tendency of the insulin derivative to self-associate to dodecamer form,
mixing the aqueous phase, the zinc ions and the zinc complex forming compound to form a pharmaceutical formulation.

83a. A process for preparing a shelf-stable pharmaceutical formulation comprising
  d) Providing an aqueous phase comprising an insulin derivative
  e) Providing more than about 4 zinc ions per 6 molecules of the insulin derivative,
  f) Providing a zinc complex forming compound to increase the tendency of the insulin derivative to self-associate to dodecamer form,
mixing the aqueous phase, the zinc ions and the zinc complex forming compound to form a pharmaceutical formulation.

84a. Process according to paragraphs 82 or 83, wherein the formulation comprises more than about 4.3 zinc atoms per 6 molecules of the insulin derivative, more than about 4.5 zinc atoms per 6 molecules of the insulin derivative, more than about 4.7 zinc atoms per 6 molecules of the insulin derivative, more than about 4.9 zinc atoms per 6 molecules of the insulin derivative, more than about 5 zinc atoms per 6 molecules of the insulin derivative, more than about 5.5 zinc atoms per 6 molecules of the insulin derivative, more than about 6.5 zinc atoms per 6 molecules of the insulin derivative, more than about 7.0 zinc atoms per 6 molecules of the insulin derivative or more than about 7.5 zinc atoms per 6 molecules of the insulin derivative.

85a. Process according to paragraphs 82-84, wherein the formulation comprises up to about 12 zinc ions per 6 molecules of the insulin derivative.

86a. Process according to paragraphs 82-85, wherein the pharmaceutical formulation comprises between about 4.3 and about 12 zinc ions per 6 molecules of the insulin derivative, between about 4.5 and about 12 zinc ions per 6 molecules of the insulin derivative, between about 4.7 and about 12 zinc ions per 6 molecules of the insulin derivative, between about 4.9 and about 12 zinc ions per 6 molecules of the insulin derivative, between about 5 and about 11.4 zinc atoms per 6 molecules of the insulin derivative, between about 5.5 and about 10 zinc atoms per 6 molecules of the insulin derivative, between about 6 and about 10.5 zinc atoms per 6 molecules of the insulin derivative, between about 6.5 and about 10 zinc atoms per 6 molecules of the insulin derivative or between about 7 and about 9 zinc atoms per 6 molecules of the insulin derivative.

87a. Process according to paragraphs 82-86, wherein the zinc atoms are mixed in the pharmaceutical formulation in two or more than two steps.

88a. Process according to paragraphs 82-87, wherein the pharmaceutical formulation is provided by mixing zinc atoms in the aqueous phase in three, four, five or six steps.

89a. Process according to paragraphs 82-88, wherein the pharmaceutical formulation is provided by mixing zinc atoms in the aqueous phase before mixing in a preservative.

90a. Process according to paragraphs 82-89, wherein the pharmaceutical formulation is provided by mixing zinc atoms in the pharmaceutical formulation after mixing in a preservative.

91a. Process according to paragraphs 82-90, the pharmaceutical formulation is provided by mixing in zinc atoms in at least two steps, wherein at least one first step comprises mixing in zinc atoms in the pharmaceutical formulation before mixing in a preservative and at least one second step comprises mixing in zinc atoms after mixing in the preservative.

92a. Process according to paragraphs 82-91, wherein the preservative is phenol and/or m-cresol.

93a. Process according to paragraphs 82-92, wherein the molar ratio between the zinc complex forming compound and zinc ions is from about 0.05 to about 10.

94a. Process according to paragraphs 82-93, wherein the molar ratio between the zinc complex forming compound and zinc ions is from about 0.1 to about 2, from about 0.1 to about 1 or from about 0.2 to about 1.

95a. Process according to paragraphs 82-94, wherein the zinc complex forming compound is present in an amount up to about 4 mM.

96a. Process according to paragraphs 82-95, wherein the zinc complex forming compound is present in an amount from about 0.05 mM to about 4 mM, from about 0.1 mM to about 2 mM or from about 0.1 to about 1.8 mM.

97a. Process according to paragraphs 82-96, wherein the zinc complex forming compound is present in an amount up to about 1 mM.

98a. Process according to paragraphs 82-97, wherein the zinc complex forming compound is present in an amount from about 0.05 mM to about 0.95 mM.

99a. Process according to paragraphs 82-98, wherein the zinc complex forming compound is present in an amount from about 0.1 mM to about 0.9 mM, from about 0.1 mM to about 0.8 mM or from about 0.1 mM to about 0.7 mM, or from about 0.1 mM to about 0.6 mM or from about 0.2 mM to about 0.9 mM or from about 0.2 mM to about 0.8 mM.

100a. Process according to paragraphs 82-99, wherein at least about 76% of the insulin derivative molecules are present as dodecamers when measured by SEC with phenol after storage at 37° C. for 4 weeks.

101a. Process according to paragraphs 82-100, wherein at least about 77%, at least about 78%, at least about 79%, at least about 80% or at least about 85%, at least about 90%, at least about 95%, at least about 98%, at least about 99%, or at least about 99.8% of the insulin molecules in the pharmaceutical formulation are present as dodecamers when measured by SEC with phenol after storage at 37° C. for 4 weeks.

102a. Process according to paragraphs 82-101, wherein up to about 5% of the insulin derivative molecules are present as monomers when measured by SEC without phenol after storage at 37° C. for 4 weeks.

103a. Process according to paragraphs 82-102, wherein up to about 4.5%, up to about 4%, up to about 3.5%, up to about 3.0%, up to about 2.5%, up to about 2.0% or up to about 1.5% of the insulin derivative molecules are present as monomers when measured by SEC without phenol after storage at 37° C. for 4 weeks.

104a. Process according to paragraphs 82-103, wherein zinc complex forming compound is citrate compounds and/or histidine compounds.

105a. Process according to paragraph 82-104, wherein the citrate compound is citric acid monohydrate.

106a. Process according to paragraphs 82-105, wherein the histidine compound is dipeptides containing histidine or tripeptides containing histidine, 107a. Process according to paragraph 104, wherein the zinc complex forming compound is L-histidine.

108a. Process according to paragraphs 82-107, wherein the insulin derivative is selected from the group consisting of insulin derivatives of human insulin, insulin derivatives of desB30 human insulin, insulin derivatives of insulin analogues, acylated human insulin, acylated desB30 human insulin, acylated insulin analogues, acylated bovine insulin and acylated porcine insulin.

109a. Process according to paragraph 82-108, wherein the insulin derivative has a substituent —W—X—Y—Z attached to the ε-amino group of a Lys residue present in the B chain of the parent insulin, the substituent being of the general formula:

—W—X—Y—Z wherein W is:
an α-amino acid residue having a carboxylic acid group in the side chain which residue forms, with one of its carboxylic acid groups, an amide group together with ε-amino group of a Lys residue present in the B chain of the parent insulin;
a chain composed of two, three or four α-amino acid residues linked together via amide carbonyl bonds, which chain—via an amide bond—is linked to an ε-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ε-amino group of a Lys residue present in the B chain of the parent insulin;

X is:
—$\underline{C}$O—;
—CH(COOH)$\underline{C}$O—;
—CO—N(CH$_2$COOH)CH$_2$$\underline{C}$O—;
—CO—N(CH$_2$COOH)CH$_2$CON(CH$_2$COOH)CH$_2$$\underline{C}$O—;
—CO—N(CH$_2$CH$_2$COOH)CH$_2$CH$_2$$\underline{C}$O—;
—CO—N(CH$_2$CH$_2$COOH)CH$_2$CH$_2$CON(CH$_2$CH$_2$COOH)CH$_2$CH$_2$$\underline{C}$O—;
—CO—NHCH(COOH)(CH$_2$)$_4$NH$\underline{C}$O—;
—CO—N(CH$_2$CH$_2$COOH)CH$_2$$\underline{C}$O—; or
—CO—N(CH$_2$COOH)CH$_2$CH$_2$$\underline{C}$O—.
that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ε-amino group of a Lys residue present in the B chain of the parent insulin;

Y is:
—(CH$_2$)$_m$— where m is an integer in the range of 6 to 32;
a divalent hydrocarbon chain comprising 1, 2 or 3 —CH═CH— groups and a number of —CH$_2$— groups sufficient to give a total number of carbon atoms in the chain in the range of 10 to 32; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H provided that when W is a covalent bond and X is —CO—, then Z is different from —COOH.

110a. Process according to paragraphs 82-109, wherein the insulin derivative is selected from the group consisting of N$^{εB29}$—(N$^α$—(HOOC(CH$_2$)$_{14}$CO)-γ-Glu) des(B30) human insulin;

$N^{\epsilon B29}$—($N^\alpha$—(HOOC(CH$_2$)$_{15}$CO)-γ-Glu) des(B30) human insulin;

$N^{\epsilon B29}$—($N^\alpha$—(HOOC(CH$_2$)$_{16}$CO)-γ-Glu) des(B30) human insulin;

$N^{\epsilon B29}$—($N^\alpha$—(HOOC(CH$_2$)$_{17}$CO)-γ-Glu) des(B30) human insulin;

$N^{\epsilon B29}$—($N^\alpha$—(HOOC(CH$_2$)$_{18}$CO)-γ-Glu) des(B30) human insulin;

$N^{\epsilon B29}$—($N^\alpha$—(HOOC(CH$_2$)$_{16}$CO)-γ-Glu-N-(γ-Glu)) des(B30) human insulin;

$N^{\epsilon B29}$—($N^\alpha$-(Asp-OC(CH$_2$)$_{16}$CO)-γ-Glu) des(B30) human insulin;

$N^{\epsilon B29}$—($N^\alpha$-(Glu-OC(CH$_2$)$_{14}$CO)-γ-Glu) des(B30) human insulin;

$N^{\epsilon B29}$—($N^\alpha$-(Glu-OC(CH$_2$)$_{14}$CO—) des(B30) human insulin;

$N^{\epsilon B29}$—($N^\alpha$-(Asp-OC(CH$_2$)$_{16}$CO—) des(B30) human insulin;

$N^{\epsilon B29}$—($N^\alpha$—(HOOC(CH$_2$)$_{16}$CO)-α-Glu-N-(β-Asp)) des(B30) human insulin;

$N^{\epsilon B29}$—($N^\alpha$-(Gly-OC(CH$_2$)$_{13}$CO)-γ-Glu) des(B30) human insulin;

$N^{\epsilon B29}$—($N^\alpha$-(Sar-OC(CH$_2$)$_{13}$CO)-γ-Glu) des(B30) human insulin;

$N^{\epsilon B29}$—($N^\alpha$—(HOOC(CH$_2$)$_{13}$CO)-γ-Glu) des(B30) human insulin;

$N^{\epsilon B29}$—($N^\alpha$(HOOC(CH$_2$)$_{13}$CO)-β-Asp) des(B30) human insulin;

$N^{\epsilon B29}$—($N^\alpha$—(HOOC(CH$_2$)$_{13}$CO)-α-Glu) des(B30) human insulin;

$N^{\epsilon B29}$—($N^\alpha$—(HOOC(CH$_2$)$_{16}$CO)-γ-D-Glu) des(B30) human insulin;

$N^{\epsilon B29}$-hexadecandioyl-γ-Glu desB30 human insulin; and $N^{\epsilon B29}$—($N^\alpha$—(HOOC(CH$_2$)$_{14}$CO)-β-D-Asp) des(B30) human insulin 111a. Process according to paragraphs 82-108, wherein the insulin derivative is $N^{\epsilon B29}$-ω-carboxy-pentadecanoyl-γ-L-glutamylamide desB30 human insulin or $N^{\epsilon B29}$-ω-carboxy-pentadecanoyl-γ-amino-butanoyl desB30 human insulin.

112a. Process according to paragraphs 82-109, wherein the pharmaceutical formulation further comprises a rapid acting insulin.

113a. Process according to paragraph 112, wherein the rapid acting insulin is AspB28 human insulin, LysB3GluB29 human insulin and/or LysB28ProB29 human insulin.

114a. Process according to paragraphs 82-113, wherein the pharmaceutical formulation further comprises one or more excipients selected from the group consisting of preservatives, buffers, stabilizers, bulking agents, carriers, isotonic agent and surfactants.

116a. Use of a pharmaceutical formulation comprising a therapeutically effective amount of an formulation comprising an insulin derivative and more than 4 zinc atoms per six molecules of the insulin derivative for the treatment of type 1 diabetes, type 2 diabetes and other states that cause hyperglycaemia in patients in need of such a treatment.

117a. Method for treating type 1, type 2 diabetes and other states that cause hyperglycaemia in patients in need of such a treatment by the use of a pharmaceutical formulation comprising an insulin derivative, more than 4 zinc atoms per 6 molecules of the insulin derivative and a zinc complex forming compound.

118a. Method according to paragraph 117, wherein zinc complex forming compound is citrate compounds and/or histidine compounds.

119a. Method according to paragraph 117-118, wherein the citrate compound is citric acid monohydrate.

120a. Method according to paragraphs 117-119, wherein the histidine compound is dipeptides containing histidine or tripeptides containing histidine, 121a. Method to paragraph 117-119, wherein the zinc complex forming compound is L-histidine.

122a. Pharmaceutical formulation as described in the examples.

EXAMPLES

Example 1

A. Pharmaceutical Formulation with Variable Zinc Concentration but without Citrate or Histidine LysB29Nε-hexadecandioyl-γ-Glu desB30 human insulin 0.6 mM, 3-6 $Zn^{2+}$/6 ins, glycerol 174 mM, phenol 16 mM, m-cresol 16 mM, NaCl 10 mM, pH 7.4:

An aqueous solution (Stock solution I) of phenol, m-cresol, glycerol and NaCl was prepared together with an aqueous solution (Stock solution II) of LysB29Nε-hexadecandioyl-γ-Glu desB30 human insulin. A fraction of Stock solution I was mixed a fraction of Stock solution II and pH was adjusted to about 7.5. Variable amounts of an aqueous 10 mM zinc acetate solution was added in fractions corresponding to the number of zinc ions per insulin molecule, pH was adjusted to 7.4 using diluted HCl/NaOH and the solution was filtered through a 0.22 µm sterile filter.

B. Pharmaceutical Formulation with Variable Histidine Concentration

LysB29Nε-hexadecandioyl-γ-Glu desB30 human insulin 0.6 mM, 6 $Zn^{2+}$/6 ins, glycerol 174 mM, phenol 16 mM, m-cresol 16 mM, NaCl 10 mM, pH 7.4, histidine 0-6 mM:

An aqueous solution (Stock solution I) of phenol, m-cresol, glycerol and NaCl was prepared together with an aqueous solution (Stock solution II) of LysB29Nε-hexadecandioyl-γ-Glu desB30 human insulin. An aqueous solution (Stock solution III) of histidine was prepared and pH was adjusted to 7.4 using diluted HCl/NaOH. A fraction of Stock solution I was mixed with variable amounts of Stock solution III and a fraction of Stock solution II was added and pH was adjusted to about 7.5. An aqueous 10 mM zinc acetate solution was added in six equal portions, pH was adjusted to 7.4 using diluted HCl/NaOH and the solution was filtered through a 0.22 µm sterile filter.

C. Pharmaceutical Formulation with Variable Citrate Concentration

LysB29Nε-hexadecandioyl-γ-Glu desB30 human insulin 0.6 mM, 6 $Zn^{2+}$/6 ins, glycerol 174 mM, phenol 16 mM, m-cresol 16 mM, NaCl 10 mM, pH 7.4, citrate 0-0.6 mM:

An aqueous solution (Stock solution I) of phenol, m-cresol, glycerol and NaCl was prepared together with an aqueous solution (Stock solution II) of LysB29Nε-hexadecandioyl-γ-Glu desB30 human insulin. An aqueous solution (Stock solution III) of citrate (citric acid, monohydrate) was prepared and pH was adjusted to 7.4 using diluted HCl/NaOH. A fraction of Stock solution I was mixed with variable amounts of Stock solution III and a fraction of Stock solution II was added and pH was adjusted to about 7.5. An aqueous 10 mM zinc acetate solution was added in six equal portions, pH was adjusted to 7.4 using diluted HCl/NaOH and the solution was filtered through a 0.22 µm sterile filter.

Example 2

The preparations from Example 1 were filled to glass cartridges and the distribution of the individual association species at formulation and post-injection conditions was estimated using the size exclusion chromatography methods described in Example 3. Samples were analysed immediately after preparation and following storage at 5 and 37° C. for 2 weeks and/or 4 weeks.

Example 3

Analytical Method A

SEC with Phenol (Formulation Conditions)

The following size exclusion chromatography method was used to assess the distribution of non-covalent associates at formulation conditions, i.e. with phenol in the eluent. A TSK-GEL Super SW2000 column was used with isocratic elution with an eluent consisting of 10 mM trishydroxymethylaminomethan, 140 mM NaCl and 2 mM phenol, pH 7.4 at room temperature and 0.3 mL/min. Results are expressed in % dodecamer and % HMWA (High Molecular Weight Associates) based on the relative peak area of the individual species.

Analytical Method B

SEC without Phenol (Post-Injection Conditions)

The following size exclusion chromatography method was used to assess the distribution of non-covalent associates at post-injection conditions, i.e. without phenol in the eluent liquid. A Superdex 200 (10/300 GL) column was used with isocratic elution with an eluent consisting of 10 mM trishydroxymethylaminomethan, 140 mM NaCl, pH 7.4 at room temperature and 0.5 mL/min. Results are expressed in % monomer based on the relative peak area of the monomer peak.

Example 4

Figure 2:
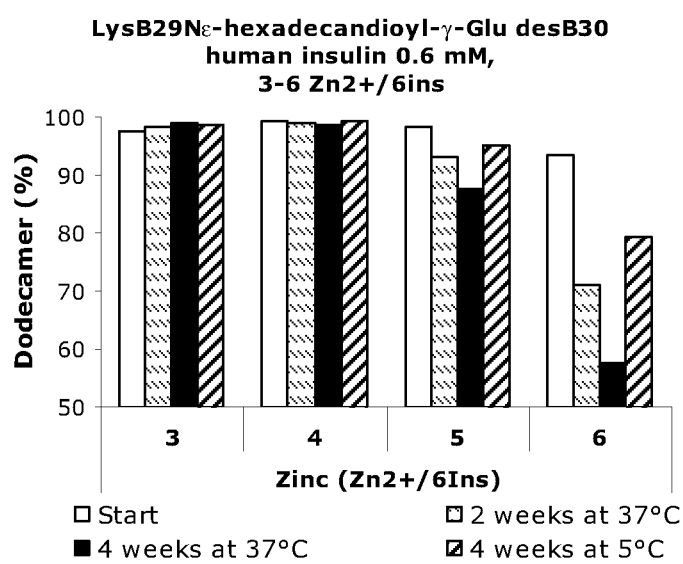
FIG. 2: Fraction of LysB29Nε-hexadecandioyl-γ-Glu desB30 human insulin as dodecamers versus zinc concentration and storage time at 5 and 37° C.
Figure 3:
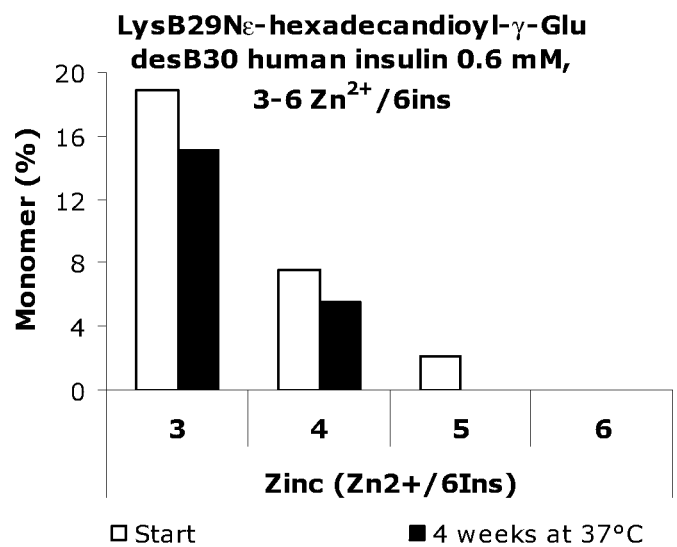
FIG. 3: Fraction of LysB29Nε-hexadecandioyl-γ-Glu desB30 human insulin as monomers versus zinc concentration and storage time at 37° C.

Preparations with zinc concentrations at 3, 4, 5 or 6 Zinc ions per 6 insulin derivatives were prepared according to Example 1A, subjected to the test conditions described in Example 2 and analyzed according to the analytical methods in Example 3A and 3B. A significant decrease in formation of HMWA and an almost concomitant increase in the amount of insulin dodecamer was observed with decreasing zinc concentration at formulation conditions (FIGS. 1 and 2, respectively). On the other hand, a significant increased formation of monomeric insulin at post-injection conditions was observed when reducing the zinc concentration (FIG. 3). Thus, formation of HMWA cannot be reduced by simply reducing the zinc concentration without formation of monomeric insulin at post-injection conditions.

Example 5

Figure 4:
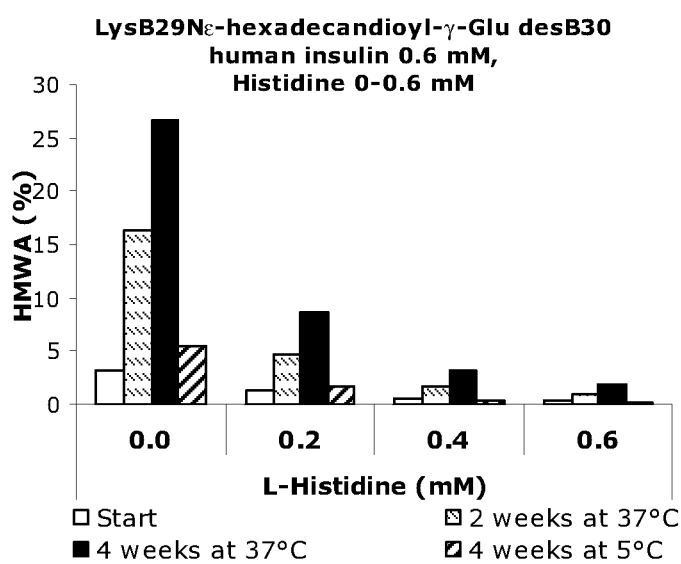
FIG. 4: Fraction of LysB29Nε-hexadecandioyl-γ-Glu desB30 human insulin as HMWA versus histidine concentration and storage time at 5 and 37° C.
Figure 5:
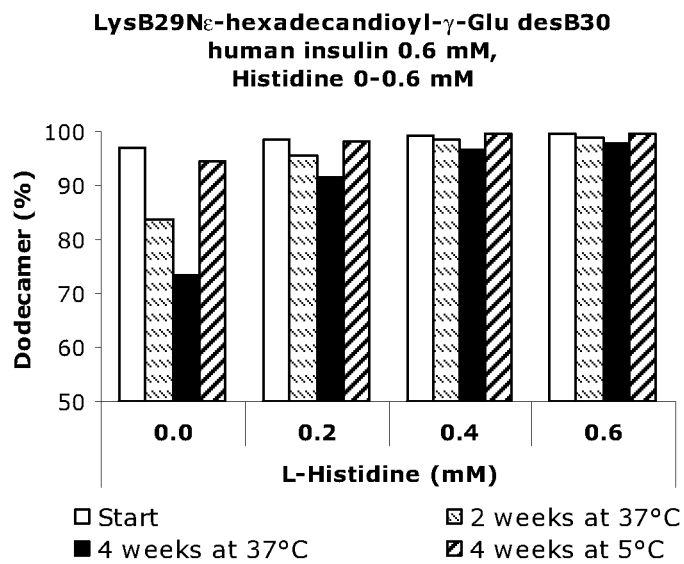
FIG. 5: Fraction of LysB29Nε-hexadecandioyl-γ-Glu desB30 human insulin as dodecamers versus histidine concentration and storage time at 5 and 37° C.
Figure 6:
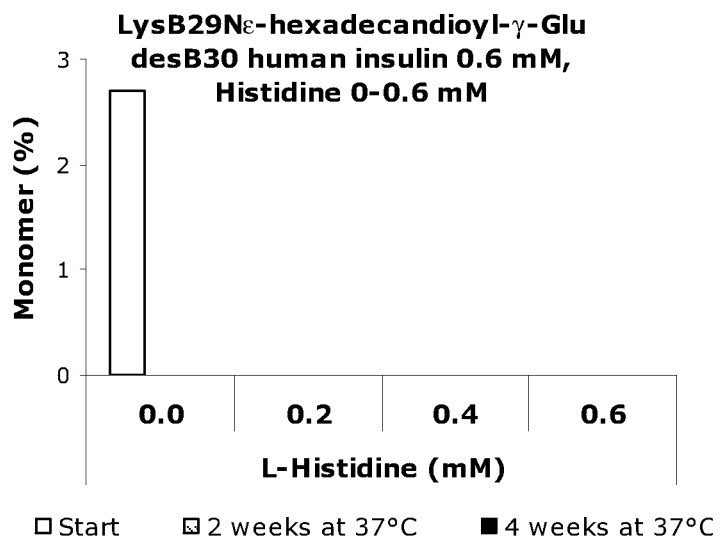
FIG. 6: Fraction of LysB29Nε-hexadecandioyl-γ-Glu desB30 human insulin as monomers versus histidine concentration and storage time at 37° C.

Preparations with histidine concentrations at 0.0 mM, 0.2 mM, 0.4 mM and 0.6 mM were prepared according to Example 1B, subjected to the test conditions described in Example 2 and analyzed according to the analytical methods in Example 3A and 3B. From FIG. 5 it is seen that a pharmaceutical formulations with 0.0 mM histidine stored for 4 weeks at 37° C., 75% of the insulin derivatives are present as dodecamers. A significant decrease in formation of HMWA and an almost concomitant increase in the amount of insulin dodecamer was observed with increasing concentration of histidine at formulation conditions (FIGS. 4 and 5, respectively). Additionally, no formation of monomeric insulin at post-injection conditions could be detected with increasing histidine concentration (FIG. 6). Thus, formation of HMWA is reduced significantly in the presence of up to 0.6 mM histidine without formation of monomeric insulin at post-injection conditions.

Example 6

Figure 7:
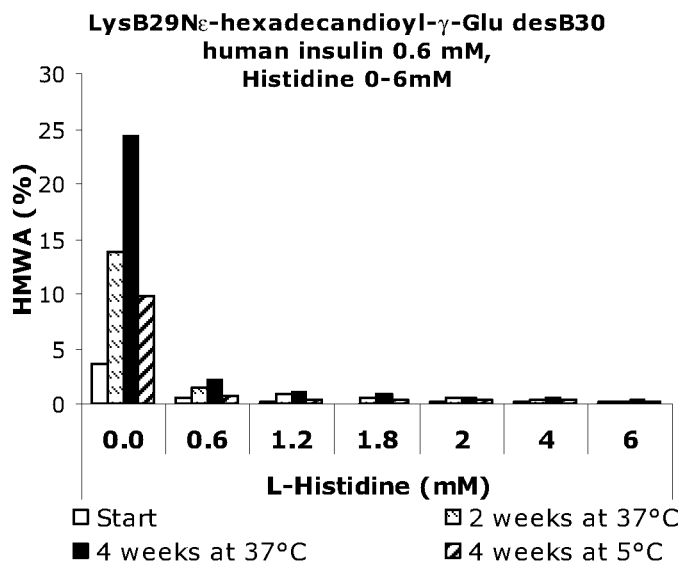
FIG. 7: Fraction of LysB29Nε-hexadecandioyl-γ-Glu desB30 human insulin as HMWA versus histidine concentration and storage time at 5 and 37° C.
Figure 8:
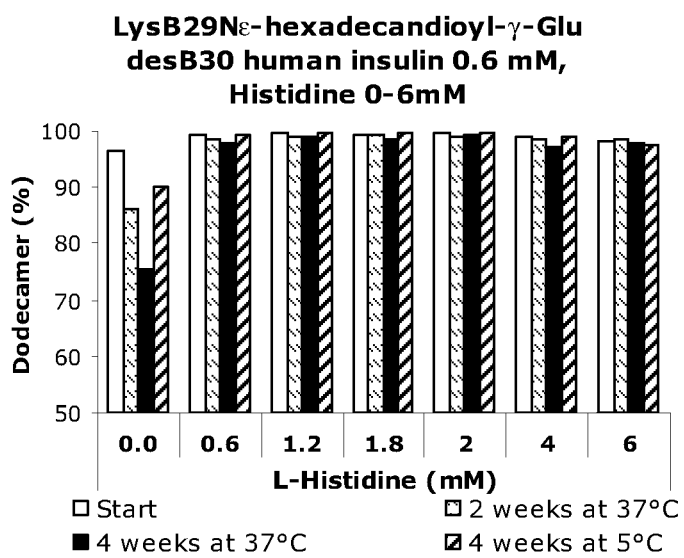
FIG. 8: Fraction of LysB29Nε-hexadecandioyl-γ-Glu desB30 human insulin as dodecamers versus histidine concentration and storage time at 5 and 37° C.
Figure 9:
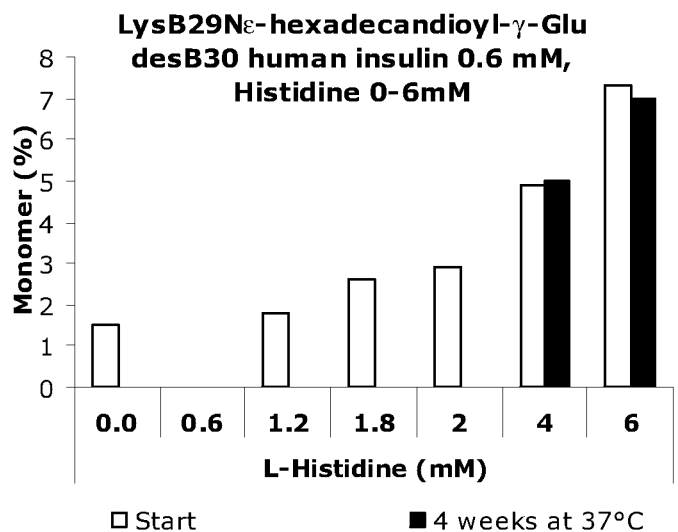
FIG. 9: Fraction of LysB29Nε-hexadecandioyl-γ-Glu desB30 human insulin as monomers versus histidine concentration and storage time at 37° C.

Preparations with histidine concentrations at 0.0 mM, 0.6 mM, 1.2 mM, 1.8 mM, 2.0 mM, 4.0 mM and 6.0 mM were prepared according to Example 1B, subjected to the test conditions described in Example 2 and analyzed according to the analytical methods in Example 3A and 3B. A significant decrease in formation of HMWA and an almost concomitant increase in the amount of insulin dodecamer was observed with increasing concentration of histidine at formulation conditions (FIGS. 7 and 8, respectively). Additionally, only moderate formation of monomeric insulin at post-injection conditions could be detected with increasing histidine concentration (FIG. 9). Thus, formation of HMWA is reduced significantly in the presence of up to 6 mM histidine without formation of major amounts of monomeric insulin at post-injection conditions.

Example 7

Figure 10:
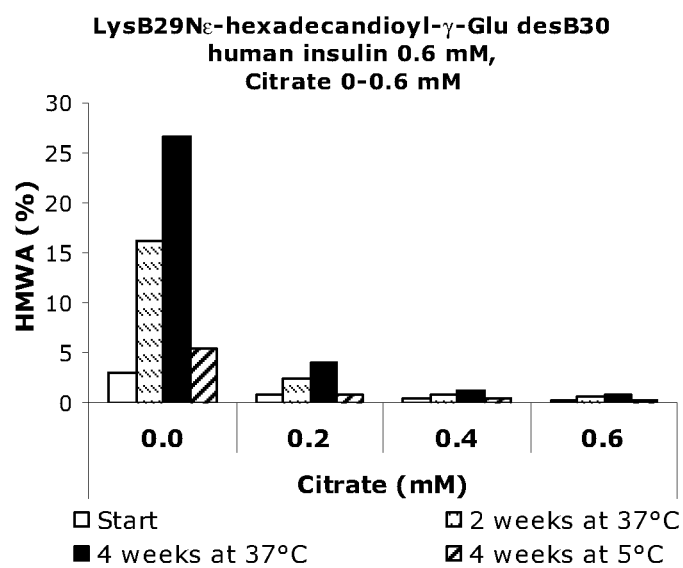
FIG. 10: Fraction of LysB29Nε-hexadecandioyl-γ-Glu desB30 human insulin as HMWA versus citrate concentration and storage time at 5 and 37° C.
Figure 11:
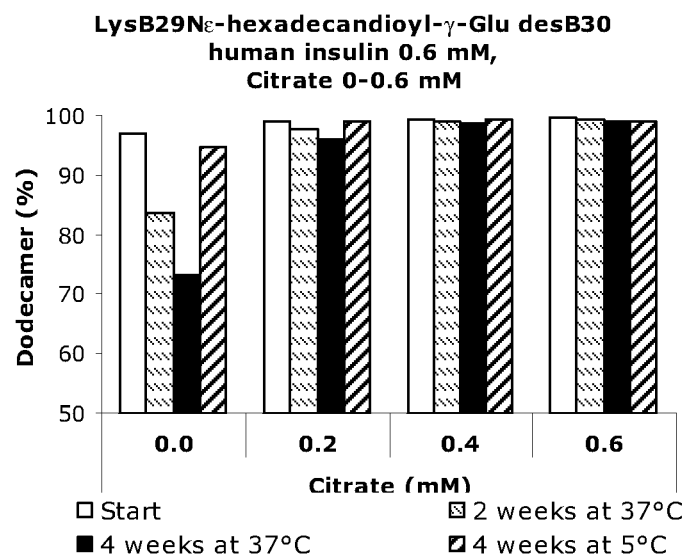
FIG. 11: Fraction of LysB29Nε-hexadecandioyl-γ-Glu desB30 human insulin as dodecamers versus citrate concentration and storage time at 5 and 37° C.
Figure 12:
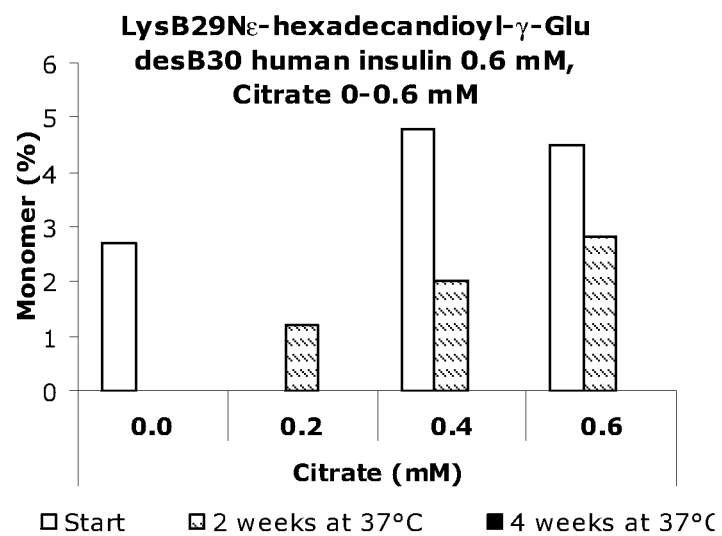
FIG. 12: Fraction of LysB29Nε-hexadecandioyl-γ-Glu desB30 human insulin as monomers versus citrate concentration and storage time at 37° C.

Preparations with citrate concentrations at 0.0 mM, 0.2 mM, 0.4 mM and 0.6 mM were prepared according to Example 1C, subjected to the test conditions described in Example 2 and analyzed according to the analytical methods in Example 3A and 3B. A significant decrease in formation of HMWA and an almost concomitant increase in the amount of insulin dodecamer was observed with increasing concentration of citrate at formulation conditions (FIGS. 10 and 11, respectively). Additionally, only moderate formation of monomeric insulin at post-injection conditions could be detected with increasing citrate concentration (FIG. 12). Thus, formation of HMWA is reduced significantly in the presence of citrate without formation of major amounts of monomeric insulin at post-injection conditions.

The invention claimed is:

1. A soluble pharmaceutical formulation comprising dodecamers of insulin derivative wherein the formulation further comprises
   a) more than 4 zinc atoms per 6 molecules of the insulin derivative,
   b) citric acid monohydrate and/or a histidine compound used in an amount sufficient to increase the tendency of the insulin derivative to self-associate into dodecamers,
   wherein the insulin derivative is a parent insulin with an ε-amino group of a Lys residue present in the B chain of the parent insulin acylated and wherein the insulin derivative can be modified from the parent insulin by up to one further modification selected from the group consisting of the addition of one amino acid to the parent insulin, deletion of one amino acid from the parent insulin or the exchange of one amino acid from the parent insulin, wherein at least about 76% of the insulin derivative molecules are present as dodecamers when measured by SEC with phenol after storage at 37° C. for 4 weeks.

2. A pharmaceutical formulation according to claim 1, wherein the molar ratio between the citric acid monohydrate and/or a histidine compound and zinc ions is from about 0.05 to about 10, from about 0.1 to about 2, from about 0.1 to about 1 or from about 0.2 to about 1.

3. A pharmaceutical formulation according to claim 1, wherein the citric acid monohydrate or the histidine compound is present in an amount from about 0.05 mM to about 4 mM, from about 0.1 mM to about 2 mM, from about 0.1 to about 1.8 mM, from about 0.05 mM to about 0.95 mM, from about 0.1 mM to about 0.9 mM, from about 0.1 mM to about 0.8 mM, from about 0.1 mM to about 0.7 mM, from about 0.1 mM to about 0.6 mM, from about 0.2 mM to about 0.9 mM or from about 0.2 mM to about 0.8 mM.

4. A pharmaceutical formulation according to claim 1, wherein at least about 77%, at least about 78%, at least about 79%, at least about 80%, at least about 85%, at least about 90%, at least about 95%, at least about 98%, at least about 99%, or at least about 99.8% of the insulin derivative molecules are present as dodecamers when measured by SEC with phenol after storage at 37° C. for 4 weeks.

5. A pharmaceutical formulation according to claim 1, wherein up to about 5%, up to about 4.5%, up to about 4%, up to about 3.5%, up to about 3.0%, up to about 2.5%, up to about 2.0% or up to about 1.5% of the insulin derivative molecules are present as monomers when measured by SEC without phenol after storage at 37° C. for 4 weeks.

6. A pharmaceutical formulation according to claim 1, wherein the formulation comprises a histidine compound.

7. A pharmaceutical formulation according to claim 1, wherein the insulin derivative has a substituent —W—X—Y—Z attached to the ϵ-amino group of a Lys residue present in the B chain of the parent insulin, the substituent being of the general formula:

—W—X—Y—Z wherein W is:
an α-amino acid residue having a carboxylic acid group in the side chain which residue forms, with one of its carboxylic acid groups, an amide group together with e ϵ-amino group of a Lys residue present in the B chain of the parent insulin;
a chain composed of two, three or four α-amino acid residues linked together via amide carbonyl bonds, which chain—via an amide bond—is linked to an ϵ-amino group of a Lys residue present in the B chain of the parent insulin, the amino acid residues of W being selected from the group of amino acid residues having a neutral side chain and amino acid residues having a carboxylic acid group in the side chain so that W has at least one amino acid residue which has a carboxylic acid group in the side chain; or
a covalent bond from X to an ϵ-amino group of a Lys residue present in the B chain of the parent insulin;

X is:
—$\underline{C}$O—;
—CH(COOH)$\underline{C}$O—;
—CO—N(CH$_2$COOH)CH$_2$$\underline{C}$O—;
—CO—N(CH$_2$COOH)CH$_2$CON(CH$_2$COOH)CH$_2$$\underline{C}$O;
—CO—N(CH$_2$CH$_2$COOH)CH$_2$CH$_2$$\underline{C}$O—;
—CO—N(CH$_2$CH$_2$COOH)CH$_2$CH$_2$CON(CH$_2$CH$_2$COOH)CH$_2$CH$_2$$\underline{C}$O—;
—CO—NHCH(COOH)(CH$_2$)$_4$NH$\underline{C}$O;
—CO—N(CH$_2$CH$_2$COOH)CH$_2$$\underline{C}$O—; or
—CO—N(CH$_2$COOH)CH$_2$CH$_2$$\underline{C}$O;

that
a) when W is an amino acid residue or a chain of amino acid residues, via a bond from the underscored carbon forms an amide bond with an amino group in W, or
b) when W is a covalent bond, via a bond from the underscored carbonyl carbon forms an amide bond with an ϵ-amino group of a Lys residue present in the B chain of the parent insulin;

Y is:
—(CH$_2$)$_m$— where m is an integer in the range of 6 to 32; or
a divalent hydrocarbon chain comprising 1, 2 or 3 —CH=CH— groups and a number of —CH$_2$— groups sufficient to give a total number of carbon atoms in the chain in the range of 10 to 32; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H; or
—PO$_3$H provided that when W is a covalent bond and X is —CO—, then Z is different from —COOH.

8. A pharmaceutical formulation according to claim 1, wherein the pharmaceutical formulation further comprises a rapid-acting insulin.

9. A process for preparing a soluble pharmaceutical formulation of claim 1 comprising
a) Providing an aqueous phase comprising an insulin derivative,
b) Providing more than about 4 zinc ions per 6 molecules of the insulin derivative,
c) Providing citric acid monohydrate and/or a histidine compound to increase the tendency of the insulin derivative to self-associate to dodecamer form, and
mixing the aqueous phase, the zinc ions and the citric acid monohydrate and/or the histidine compound to form a soluble pharmaceutical formulation.

10. The process of claim 9 wherein the resulting soluble pharmaceutical formulation is shelf stable.

11. A pharmaceutical composition according to claim 1, wherein the ϵ-amino group of the Lys B29 insulin derivative is acylated.

12. A pharmaceutical composition according to claim 1, where the insulin derivative is LysB29Nϵ-hexadecandioyl-γ-Glu desB30 human insulin.

13. A method of treatment of type 1 diabetes, type 2 diabetes, and other disease states or conditions that cause hyperglycaemia, comprising administering to a subject in need of such treatment a pharmaceutically effective amount of a pharmaceutical formulation according to claim 1.

14. A soluble pharmaceutical formulation according to claim 1, wherein the formulation is shelf stable.

* * * * *